United States Patent [19]

Babcock et al.

[11] 4,297,350
[45] Oct. 27, 1981

[54] MALE CONTRACEPTIVE STEROIDS AND METHODS OF USE

[75] Inventors: John C. Babcock; J. Allan Campbell, both of Kalamazoo; Thomas J. Lobl, Portage, all of Mich.

[73] Assignee: The Upjohn Company, Kalamazoo, Mich.

[21] Appl. No.: 949,797

[22] Filed: Oct. 10, 1978

[51] Int. Cl.$^3$ ............................................. A61K 31/56
[52] U.S. Cl. .................................. 424/238; 424/241; 424/243; 260/239.5; 260/397.4; 260/239.55 C; 260/239.55 R
[58] Field of Search ............... 424/241; 260/397.4, 260/397.5, 397.45

[56] References Cited

U.S. PATENT DOCUMENTS

| | | | |
|---|---|---|---|
| 3,980,638 | 9/1976 | Babcock et al. | 424/241 |
| 4,016,269 | 4/1977 | Hofmeister et al. | 260/397.4 |
| 4,052,421 | 10/1977 | Biollaz et al. | 260/397.4 |
| 4,053,489 | 10/1977 | Wirth | 260/397.5 |
| 4,105,761 | 8/1978 | Pierdet et al. | 260/397.5 |

Primary Examiner—Elbert L. Roberts
Attorney, Agent, or Firm—Bruce Stein

[57] ABSTRACT

The steroids of the present invention have been found to be useful as male contraceptives when administered orally. Upon cessation of administration of the male contraceptive steroids of the present invention the male promptly regains normal fertility.

17 Claims, No Drawings

MALE CONTRACEPTIVE STEROIDS AND METHODS OF USE

BACKGROUND OF THE INVENTION

Most forms of reversible contraception are practiced by the female member of an animal pair, whether the animal be human or not. With humans, physical (diaphragm and IUD) and chemicl ("the Pill", vaginal creams, foams, ointments, etc.) methods are available. At present there are only two acceptable methods for the human male. These are the condom and bilateral vasectomy. With the condom the failure rate is high, resulting in unwanted pregnancies. Vasectomies for practical purposes must be considered irreversible. Therefore, a method of male human contraception which is both reversible and reliable is highly desirable.

With regards to the non-human mammals a male contraceptive is also highly desirable. For non-domestic commercial animals such as horses, cattle, sheep, etc., the present situation is to separate male and female animals so the female may be selectively, artificially inseminated. It would, of course, be simpler to permit the animals to cohabitate under circumstances where the female cannot become pregnant. Domestic animals normally cohabitate because it is virtually impossible to separate male and female cats and dogs in a household. Many times it would be desirable to be able to prevent unwanted pregnancies of domestic animals under cohabitation circumstances. Additionally, with undesirable rodents a male contraceptive would be helpful to decrease fertility and thereby decrease or eliminate the number of undesirable rodents.

H. J. Ringold et al. in J. Am. Chem. Soc. 81, 427 (1959) disclose 17β-hydroxy-2α-methyl-5α-androstances in general and in particular 17β-hydroxy-2α-methyl-5α-androstan-3-one and 17β-hydroxy-2α,17α-dimethyl-5α-androstan-3-one. U.S. Pat. No. 2,852,537 discloses 2α-alkyl-17β-hydroxy-17α-vinyl and -17α-ethinylandrost-4-ene-3-one type compounds and their anti-androgenic properties. R. Youssefyeh in Tetrahedron Letters 2161 (1964) discloses some 2α-methyl and ethyl-17β-hydroxy-5α-androstan-3-ones. U.S. Pat. No. 3,846,456 discloses 17β-hydroxy-2α,7α-dimethylandrost-4-en-3-one and its use as an anti-fertility agent but without stating anti-fertility in the male or female.

17β-Methoxy-5α-androstan-3-one is known, see U.S. Pat. No. 3,301,850, Example 14. 17β-Cyclopentyloxy-5α-androstan-3-one is also known, see British Pat. No. 1,327,910.

The 2-spirocyclopropyl androstanes are known, see Chem. Ber. 1470 (1965) and French Pat. No. 1,384,279.

R. Weichert and E. Kaspar in Chem. Ber., 93, 1710 (1960) disclose 17β-hydroxy and 17β-acetoxy-1α,2α-methylene-5α-androstan-3-one. V. Mende et al. in Tetrahedron Letters 629 (1975) also disclose 17β-acetoxy-1α,2α-methylene-5α-androstan-3-one. German Patent 1,961,906 discloses 17β-hydroxy- and 17β-acyloxy-7α-methyl-1α,2α-methyleneandrost-4-en-3-one.

Both 17β-hydroxy and 17β-acetoxy-2-methyl-5α-androst-1-en-3-one are known, see J. Am. Chem. Soc. 82, 5494 (1960). The unsaturated compound 17β-hydroxy-1-methyl-5α-androst-1-en-3-one is also known, see Arzneimittel Forschung 12, 218 (1962).

U.S. Pat. No. 3,415,816 discloses a process to prepare 17β-hydroxy-5α-androstan-2-one and esters thereof. 17β-Hydroxy-3β-methyl-5α-androstan-2-one is disclosed in Steroids 27, 581 (1976).

P. D. Klimstra and R. E. Counsell in J. Med. Pharm. Chem. 5, 1216 (1962) disclose 2α-fluoro-17β-hydroxy-5α-androstan-3-one. J. Edwards and H. J. Ringold in J. Am. Chem. Soc. 81, 5262 (1959) disclose 2α-fluoro-17β-hydroxy-17α-methyl-5α-androstan-3-one. B. Ellis and V. Petrow in J. Chem. Soc. 3869 (1953) disclose a 2-chloro steroid, 2-chlorocholestan-3-one, see also J. Am. Chem. Soc. 75, 3500 (1953). U.S. Pat. No. 3,301,850 (Example 15) discloses 2α-bromo-17β-methoxy-5α-androstan-3-one.

C. W. Shoppee in J. Chem. Soc. 1138 (1946) disclosed 3α- and 3β-chloro-5α-androstan-17-ones. There is no disclosure of 3-chloro-17β-hydroxy-5α-androstanes nor of their 17-ethers.

G. Ohta et al. in Chem. Pharm. Bull. 16, 1487 (1968) reported the synthesis of 17β-hydroxy-2'-methyl-5α-androstano[2,3-d]oxazole as well as the 17-acetate. P. DeRuggieri et al. very comprehensively reviewed the heterocyclic steroids in Farmaco Ed. Sci. 20, 280 (1965); no mention was made of [2,3-d]oxazole steroids. 17β-Methoxy-5α-androst-2-en[2,3-d]isoxazole is known, see U.S. Pat. No. 3,980,638.

U.S. Pat. No. 3,704,295 discloses 17β-hydroxy-5α-androstano[3,2-c]pyrazole (Example 6b) as well as 17β-hydroxyandrost-4-eno[3,2-c]pyrazole (Example 9b). The 17α-methyl analogs, 17β-hydroxy-17α-methyl-5α-androstano[3,2-c]pyrazole and 17β-hydroxy-17α-methylandrost-4-eno[3,2-c]pyrazole are disclosed in J. Am. Chem. Soc. 71, 1513 (1959). U.S. Pat. No. 3,704,295 claims various [3,2-c]pyrazoles of the androstane series which are substituted on the pyrazole ring though few examples are given. S. Hayashi and T. Komeno in Chem. Pharm. Bull. 17, 1319 (1969) disclose 5'-aryl-5α-androstano[3,2-c]pyrazoles. U.S. Pat. No. 3,539,556 discloses 2'-aryl-17α-ethynyl-17β-hydroxyandrostan-4-eno[3,2-c]pyrazoles. Two examples, Examples 13 and 14 disclose tetrahydropyranyl ethers. These compounds were disclosed as useful anti-inflammatory agents.

U.S. Pat. No. 3,030,358 discloses a reductive process for the transformation of androst-4-eno[3,2-c]pyrazoles to the corresponding androstano[3,2-c]pyrazole.

J. A. Zderic et al. in Chem. Ind. 1625 (1960) disclose 17β-hydroxy-17α-methyl-5α-androstano[3,2-b]thiazole.

H. J. Ringold et al. in J. Am. Chem. Soc. 81, 427 (1959), and U.S. Pat. No. 3,135,743 both disclose various 2-hydroxymethylene-17β-hydroxyandrostanes with and without unsaturation at $C_4$ and with various substituents at the 17α-position such as hydrogen, methyl, ethyl and vinyl. U.S. Pat. No. 3,980,638, Example 3, discloses 17β-methoxy-2-hydroxymethylene-5α-androstan-3-one. The 2-hydroxymethylene steroids were useful as intermediates in the production of steroido[2,3-d]isoxazoles.

Genkichi Ohta et al. in Chem. Pharm. Bull. 16, 1487 (1968) reported synthesis of 17β-hydroxy-5α-androstano-[2,3-d]imidazole the 2'-methyl, and the 2'-methyl-17-acetate derivatives.

U.S. Pat. Nos. 3,026,317 and 3,132,137 both disclose 17β-hydroxy-5α-androstane and androst-4-ene[3,2-d]pyrimidines and 17-acrylates thereof.

U.S. Pat. No. 3,301,850 discloses 2α,3α-thioepoxides of 5α-androstanes. Example 8 discloses the 17-tetrahydropyranyl ether; Example 17 the 17-methyl ether; and Example 19 the 17-ethyl ether. The utility disclosed for these compounds is as hormonal agents as evidenced by their anabolic properties and possessing the particular advantage of exhibiting only minimal anti-fertility side effects. The 2α,3α-epithio-5α-androstane 17-ethers (XV) of the present invention are useful as male contraceptive agents. U.S. Pat. No. 3,169,136, in particular Example 1, discloses a process to prepare 2α,3α-epoxy-5α-androstanes. In U.S. Pat. No. 3,169,136 the 2α,3α-epoxy-5α-androstanes are used as intermediates to prepare 2β-halo-5α-androstanes. U.S. Pat. No. 3,682,898 discloses 17β-hydroxy-2α,3α-epoxy- and 2α,3α-epithio-7α-methyl-5α-androstanes and esters thereof.

The oximes of 3-keto steroids are well known. U.S. Pat. No. 3,686,237 and A. F. Hirsh et al. in J. Med. Chem. 20, 1546 (1977) describe O-aryloximes of 3-keto androstanes. The oximes and O-substituted oximes of the 3-keto steroid 17-ethers (I-IV and VI) of the present invention are novel.

The various steroids discussed above were generally 17β-hydroxy or 17-acrylates thereof. With the thio-epoxides the utility alleged was hormonal ". . . and possess the particular advantage of exhibiting only minimal . . . anti-fertility side-effects." The epithio 17-ethers (XV) of the present invention are just the opposite: they are useful as male contraceptive agents. With the pyrazoles, U.S. Pat. No. 3,539,556 claims 17β-hydroxy and 17-acyloxy steroido[3,2-c]pyrazoles. However, Examples 13 and 14 disclose tetrahydropyranyl ethers. Those ethers are not within the scope of the present invention, the tetrahydropyranyl ether group is very labile and following absorption it is readily lost while the ether groups of the present invention are retained for a much greater length of time.

Surprisingly and unexpectedly the 17-ethers of the present invention are useful as reversible male contraceptives upon oral administration.

SUMMARY OF THE INVENTION

Disclosed are steroidal androstane or androstene 17-ethers (I-XV) which are useful as male contraceptives when administered orally in a contraceptively effective amount to a mammal post-puberty.

Also disclosed are pharmaceutical compositions for oral administration which comprise a contraceptively effective amount of a compound (I-XV) and appropriate pharmaceutical carriers.

Further disclosed is the method of male contraception which comprises oral administration of a contraceptively effective amount of a compound of the formula (I-XV) to a male mammal post-puberty selected from the group consisting of man, male dog, tom, bull, stallion, ram, boar, male rat and male mouse.

DETAILED DESCRIPTION OF THE INVENTION

The compounds of the present invention are selected from the group consisting of compounds of the formulas:

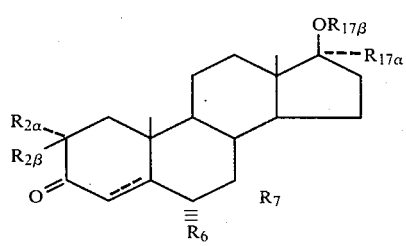
I

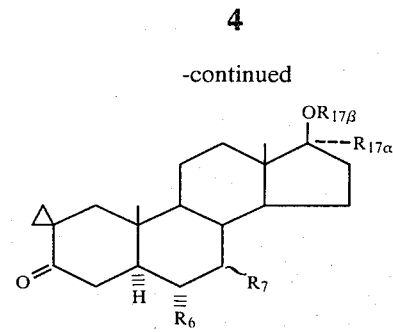
II

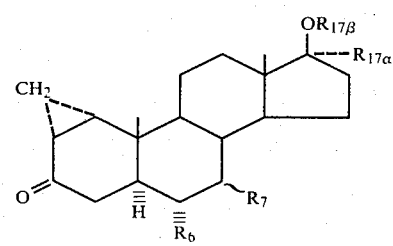
III

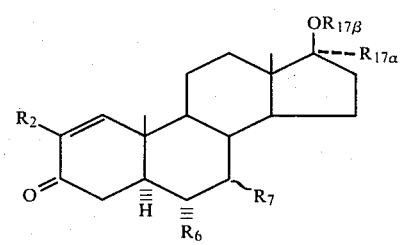
IV

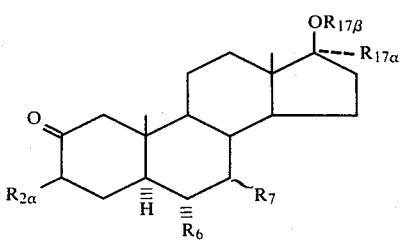
V

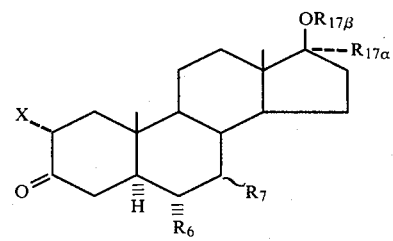
VI

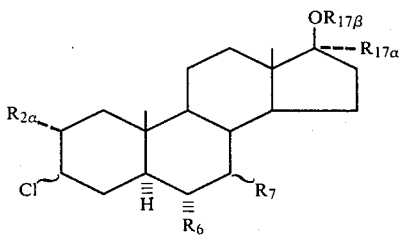
VII

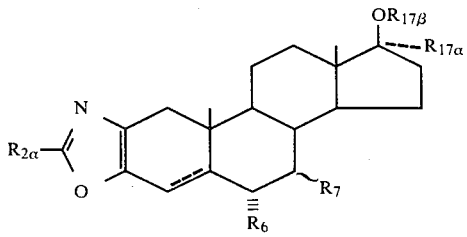
VIII

-continued

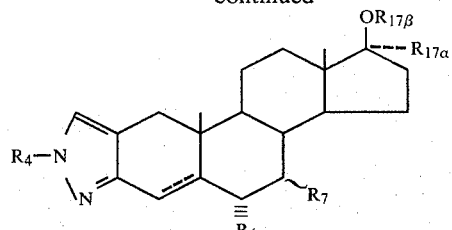  IX

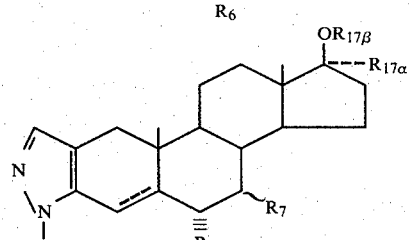  X

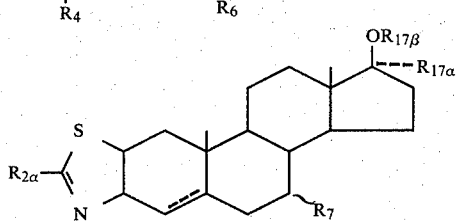  XI

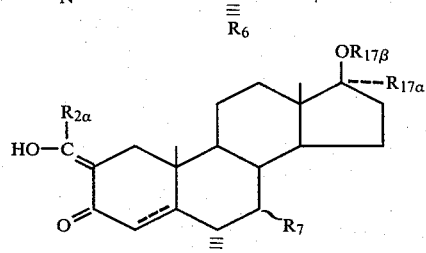  XII

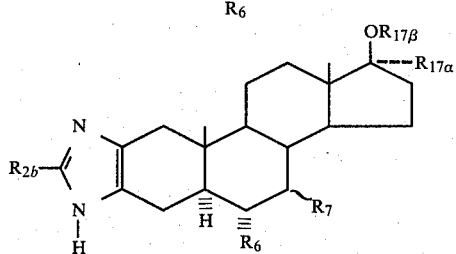  XIII

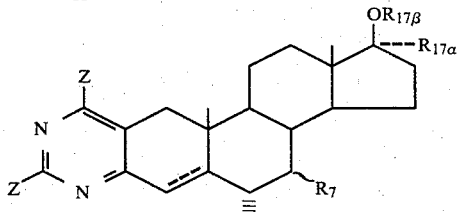  XIV

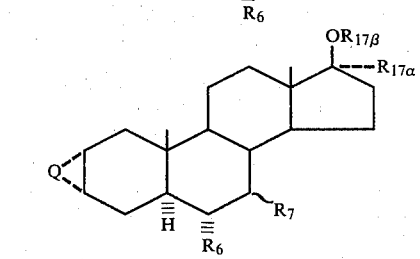  XV where A is a methyl, methoxy, trifluoromethyl, hydroxyl or nitro group or a hydrogen, fluorine, chlorine or bromine atom; where D is a methyl, methoxy, trifluoromethyl, hydroxyl or nitro group or a hydrogen, fluorine, chlorine or bromine atom; where M is a methyl, methoxy, trifluoromethyl, hydroxyl or nitro group or a hydrogen, fluorine, chlorine or bromine atom; where $R_2$ is a hydrogen atom or methyl group; where $R_{2\alpha}$ is a hydrogen atom, alkyl 1 thru 4 carbon atoms or benzyl; where $R_{2\beta}$ is a hydrogen atom or methyl group with the proviso that when $R_{2\beta}$ is methyl, $R_{2\alpha}$ is also methyl; where $R_{2a}$ is alkyl of 1 thru 3 carbon atoms or

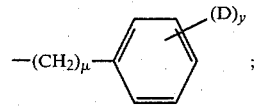  X where $R_{2b}$ is $R_{2a}$, —SH, —SCH$_3$ or amino; where $R_5$ is alkyl of 1 thru 4 carbon atoms or phenyl; where $R_4$ is $R_{2a}$ or phenyl; where $R_6$ is a hydrogen atom or methyl group; where $R_7$ is a hydrogen atom or methyl group; where $R_{17\alpha}$ is a hydrogen atom, alkyl of 1 thru 4 carbon atoms, alkenyl of 2 thru 4 carbon atoms or alkynyl of 2 thru 4 carbon atoms; where $R_{17\beta}$ is alkyl of 1 thru 16 carbon atoms,

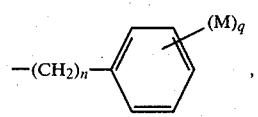

—(CH$_2$)$_n$—CH(CH$_2$)$_m$, —CH$_2$—alkenyl where alkenyl is 2 thru 15 carbon atoms or —CH$_2$—C≡CH, and $R_{17\alpha}$ and $R_{17\beta}$ can be connected to form a cyclic ether containing 4 or 5 carbon atoms; where Q is an oxygen or sulfur atom; where X is a fluorine, chlorine or bromine atom; where Z is a hydrogen atom, alkyl of 1 thru 4 carbon atoms or

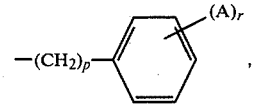

that for the compounds of formula (XIV) the Z's may be the same or different; where m is 4 thru 6; where n is 0 thru 4; where p is 0 thru 4; where q is 1 or 2, when q is 2 the M's can be the same or different; where r is 1 or 2, when r is 2 the A's can be the same or different; where y is 1 or 2, when y is 2 the D's can be the same or different; where μ is 0 thru 4; where ~ indicates the attached group can be in either the α or β configuration; and where===is a single or double bond, if a single bond the hydrogen atom at C$_5$ is α; including the oximes and O-substituted oximes of compounds I thru IV and VI made with NH$_2$-OR$_3$; with the provisos that (a) with the compounds of formula (I) $R_{17\beta}$ is not methyl when $R_{2\alpha}$, $R_{2\beta}$, $R_6$, $R_7$, and $R_{17\alpha}$ are all hydrogen, and $R_{17\beta}$ is not methyl when $R_{2\alpha}$ is methyl and $R_{2\beta}$. $R_6$, $R_7$ and $R_{17\alpha}$ are all hydrogen atoms and when ===is a single bond, (b) with the compounds of formula (VI) $R_{17\beta}$ is not methyl when $R_6$, $R_7$ and $R_{17\alpha}$ are hydrogen and X is bromine, (c) with the compounds of formula (IX) $R_{17\beta}$ is not methyl when $R_{17\alpha}$ is methyl, $R_6$, $R_7$, $R_4$ are all hydrogen and===is a single bond, and (d) with the compounds of formula (XV) when Q is a sulfur atom, $R_{17\alpha}$ is not a hydrogen atom.

The $C_{17}$ ethers of the present invention are of three types, (A) where $R_{17\alpha}$ is a hydrogen thereby providing a secondary alcohol group at $C_{17}$, (B) where $R_{17\alpha}$ is not a hydrogen atom thereby providing a tertiary alcohol group at $C_{17}$ and (C) where $R_{17\alpha}$ and $R_{17\beta}$ are taken together to form a cyclic ether

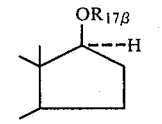  (A)

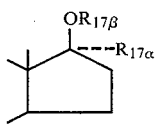  (B)

and

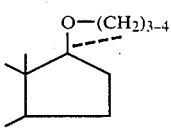  (C)

The A ring of the steroids of the present invention include the following:

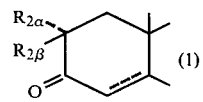 (1)  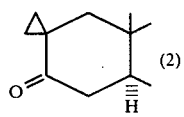 (2)

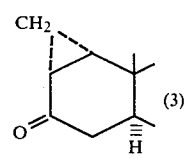 (3)  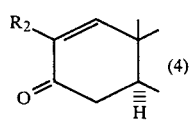 (4)

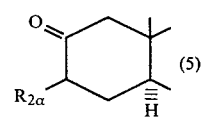 (5)  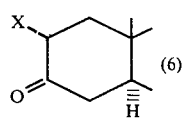 (6)

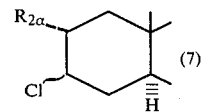 (7)  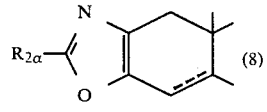 (8)

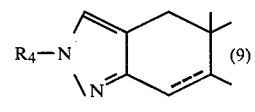 (9)  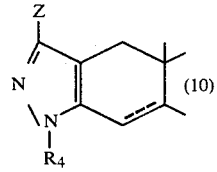 (10)

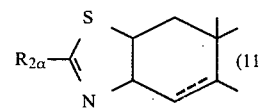 (11)  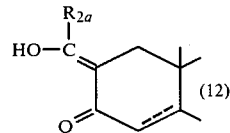 (12)

-continued

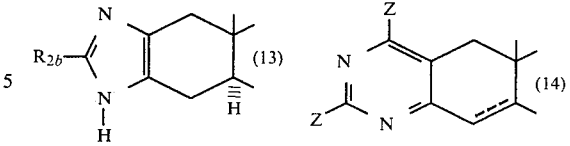 (13) (14)

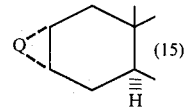 (15)

Generally the androstane-type compounds of A rings (1) thru (15) are known where at $C_{17}$ in the D ring there is a hydroxyl group (either free or esterified) in the β-position. The male contraceptive steroids of the present invention have an ether group at $C_{17}$.

The compounds of the invention (I-XV) are prepared by methods well known to those skilled in the art from 17β-hydroxy steroids which are either known or which can be readily prepared from known steroids by methods well known to those skilled in the art.

The $C_{17}$ ethers (I-XV) of the present invention are prepared from the corresponding 17β-hydroxy compounds by methods well known to those skilled in the art for preparing ethers from the corresponding alcohols. The 17β-hydroxy starting materials are well known to those skilled in the art. In fact, virtually all the references discussed in the Background of the Invention refer to 17β-hydroxy steroids. In many instances it is advisable to protect the 3-keto group of the compounds of the present invention by prior formation of a ketal, by reaction of the 3-keto steroid with ethylene glycol as is well known to those skilled in the art to form the corresponding 3-ketal. The 3-ketal may then be reacted by known methods to form the $C_{17}$-ether and the ketal hydrolyzed by known methods to obtain the 3-keto-17-ether type compound. The $C_{17}$ ethers can be prepared by alkylation of the hydroxy group. For this purpose diazoalkanes may be employed. Preferably in the presence of a Lewis acid, e.g., boron trifluoride etherate, aluminum chloride or fluoboric acid. When $R_{17\beta}$ is methyl, diazomethane is employed, see Fieser et al. "Reagents for Organic Synthesis", John Wiley and Sons, Inc., New York (1967), at page 191. Other $R_{17\beta}$ ethers are formed by using the corresponding diazoalkanes. For example, diazoethane and diazobutane produce the corresponding steroids where $R_{17\beta}$ is ethyl or butyl, respectively. The reaction is carried out by mixing a solution of the diazoalkane in a suitable, inert solvent preferably diethyl ether with the 17β-hydroxy compounds. Generally the reaction proceeds at about 25°. Diazoalkanes are well known in the art and can be prepared by methods well known in the art, see for example, Organic Reactions, John Wiley and Sons, Inc., New York Vol. 8 (1954), pages 389–394.

Another method for the alkylation of the 17β-hydroxy group is by reaction with an alcohol in the presence of boron trifluoride etherate. Thus, methanol and boron trifluoride etherate yields the methyl ether where $R_{17\beta}$ is methyl. The reaction is performed at about 25° and is conveniently followed by TLC.

Yet another method for the alkylation of the $C_{17}$ hydroxy group is by reaction with an $R_{17\beta}$-halide, preferably the iodide, e.g., methyl iodide, ethyl iodide, allyl iodide, in the presence of a base such as a metal oxide, metal alkoxide or hydroxide, e.g., barium oxide, silver oxide, potassium t-butoxide or barium hydroxide or sodium hydroxide. An inert solvent may be beneficial, e.g., benzene or dimethylformamide. The reactants are preferably stirred together and maintained at a temperature of about 25°–75°, see for example U.S. Pat. No. 3,301,850 in particular Example 14 where methyl iodide in the presence of potassium tertiary butoxide was used to form 17$\beta$-methoxy-5$\alpha$-androstan-3-one. See also U.S. Pat. No. 3,980,638, Examples 1 and 2.

Steroidal 17-ethers are conveniently prepared by phase transfer catalysis type reactions. These reactions require an aqueous phase containing a strong base and an organic phase containing the steroidal alcohol, the halide of the etherifying moiety and a quaternary ammonium salt. The aqueous phase is usually 50% sodium hydroxide and the organic phase can be the organic halide, if a liquid, or the organic halide in an inert organic diluent such as toluene, hexane, cyclohexane, etc. The preferred catalyst is tetrabutylammonium bisulfate or benzyltrimethylammonium chloride. The reaction is conveniently monitored by TLC. See Example 9.

The above procedures for forming the $C_{17}$ ethers of the present invention are useful in the cases where $R_{17\alpha}$ is a hydrogen atom (secondary alcohol) or where $R_{17\alpha}$ is not a hydrogen atom (tertiary alcohol).

The third type of ethers of the present invention, the cyclic ethers, are formed from the corresponding 17-keto compound by the process of U.S. Pat. No. 4,054,563 and the references disclosed therein.

In the case where $R_{17\alpha}$ is alkyl such as ethyl, propyl, and butyl, these compounds can be produced in many instances by reduction of an olefinic side chain at $C_{17\alpha}$, see U.S. Pat. No. 2,721,871. In the situation where the $R_{17\alpha}$ side chain is alkenyl, these compounds can be produced from the corresponding 17-keto compound by a Grignard reaction or by reduction of the corresponding alkynyl compound as set forth in J. Am. Chem. Soc. 75, 4117 (1953) and J. Am. Chem. Soc. 77, 148 (1955). The preparation of the compounds of the present invention where $R_{17\alpha}$ is alkenyl and alkynyl can be produced by the process disclosed in U.S. Pat. No. 2,838,530.

U.S. Pat. No. 3,341,557 discloses the introduction of both the 7$\alpha$-methyl and 7$\beta$-methyl groups into testosterone type compounds.

The 6$\alpha$-methyl steroids are prepared by the processes of U.S. Pat. Nos. 3,114,750, 3,116,551, 3,147,290, and an article in J. Am. Chem. Soc. 80, 2904 (1958).

The 2$\alpha$-alkyl steroids (1) can be prepared by the processes disclosed in J. Org. Chem. 21, 1333 (1956); Tetrahedron Letters 2161 (1964) and J. Am. Chem. Soc. 81, 427 (1959). In addition, U.S. Pat. No. 2,852,537 discloses a process to produce 2$\alpha$-alkyl-17$\alpha$-ethinyl steroids where the A ring is of type (1) and the D ring is of type (B).

In preparing the 2$\alpha$-alkyl steroid 17-ethers (I), the 17$\beta$-hydroxy group may be etherified before or after the addition of the 2$\alpha$-alkyl group.

The 2,2-dialkyl steroids (I) in particular the 2,2-dimethyl compounds can be prepared starting with 2-methyl-2'-formyl-5$\alpha$-androstan-3-one (U.S. Pat. No. 3,118,915, Example V) and subjecting it to the following reaction sequence: protection of the 3-ketone, for example as the ketal, reduction of the 2'-formyl group followed by regeneration of the 3-ketone.

The 2-spirocyclopropyl substituent (2) is produced by starting with the desired androstan-3-one 17-ether and reacting it with an oxalate ester in the presence of strong base. The product of this reaction, a glyoxalate, is then reacted with a base such as lithium hydride, and formaldehyde to produce the 2-methylene-3-keto-androstane 17-ether. The 2-methylene-5$\alpha$-androstan-3-one 17-ether is then reacted with diazomethane to produce the intermediate pyrazoline which upon heating produces the desired 2-spirocyclopropyl-5$\alpha$-androstan-3-one 17-ether (II). See also the procedures disclosed in French Pat. No. 1,384,279 and Chem. Ber. 1470 (1965).

Both Tetrahedron Letters 629 (1975) and Chem. Ber. 93, 1710 (1960) disclose how to prepare 1$\alpha$,2$\alpha$-methylene-5$\alpha$-androstan-3-ones (3). The 17$\beta$-hydroxy group can be etherified before or after the addition of the 1$\alpha$,2$\alpha$-methylene group to produce the 1$\alpha$,2$\alpha$-methylene-5$\alpha$-androstan-3-one 17-ethers (III).

The 2-alkyl-5$\alpha$-androst-1-en-3-one (4) can be prepared from the corresponding 2$\alpha$-alkyl-5$\alpha$-androstan-3-one (1) by the process disclosed in J. Am. Chem. Soc. 82, 5494 (1960). The 17$\beta$-hydroxy group may be etherified before or after the introduction of the $C_1$ double bond.

The 5$\alpha$-androstan-2-ones (V) of the present invention are prepared by methods well known to those skilled in the art, see Steroids, Fieser and Fieser, Reinhold Publishing Corp., New York, 1959, page 304; L. Ruzieka et al., Helv. Chem. Acta., 27, 524 (1944) and U.S. Pat. No. 3,415,816. The 17$\beta$-hydroxy group can be etherified either before or after the formation of the 2-keto group. The 3-alkylated-5$\alpha$-androstan-2-ones (V) can be prepared similarly to the 2$\alpha$-alkylated-5$\alpha$-androstan-3-ones (I). The 3-alkylated-5$\alpha$-androstan-2-ones (V) are prepared by first forming the 5$\alpha$-androstan-2-one where $R_{2\alpha}$ is a hydrogen atom. $R_{2\alpha}$ is then replaced by the desired alkyl substituent by taking advantage of the acidic nature of the proton alpha to the 2-oxo group. Alkylation of ketones on the alpha carbon atom is well known to those skilled in the art.

Processes to produce 2$\alpha$-chloro- and 2$\alpha$-bromo-5$\alpha$-androstane-type compounds (6) are well known to those skilled in the art. See J. Am. Chem. Soc. 81, 5262 (1959) for 2$\alpha$-fluoro; J. Chem. Soc. 3847 (1957) for 2$\alpha$-chloro and 2$\alpha$-bromo and in particular U.S. Pat. No. 3,055,916 discloses a process to produce 2$\alpha$-bromo-17$\beta$-hydroxy-5$\alpha$-androsta-3-one. The 17$\beta$-hydroxyl should be etherified before the introduction of the chlorine or bromine atom at $C_2$. A process to introduce a chlorine atom into a 3-keto steroid to produce a 2$\alpha$-chloro-3-keto steroid is disclosed in J. Am. Chem. Soc. 75, 3500 (1953).

A process for producing 3$\alpha$- and 3$\beta$-chloro steroids (7) from 3-hydroxy steroids is disclosed in J. Chem. Soc. 1138 (1946). If the starting material had a free 17$\beta$-hydroxyl group it would have to be protected as is well known to those skilled in the art. Alternatively, if one starts with a 3-hydroxy-17$\beta$-alkoxy-5$\alpha$-androstane, after chlorination the product is the desired 3-chloro-17$\beta$-alkoxy-5$\alpha$-androstane (VII). The 2$\alpha$-alkyl-3-chloro steroids (7) where $R_{2\alpha}$ is not a hydrogen atom are prepared by starting with the corresponding 2$\alpha$-alkyl-5$\alpha$-androstan-3-one (I) and reducing it to the corresponding 2$\alpha$-alkyl-3-hydroxy-5$\alpha$-androstane by reaction with a reducing agent such as sodium borohydride as is well known to those skilled in the art. The 2$\alpha$-alkyl-3-hydroxy-5$\alpha$-androstane is then converted to a 2$\alpha$-alkyl-3-chloro-5$\alpha$-androstane (7).

The 17β-alkoxy[2,3-d]oxazoles (VIII) are most advantageously prepared from the corresponding 17β-hydroxy-5α-androstan-3-one or -androst-4-en-3-one by first forming the desired ether at the 17β-position and then forming the [2,3-d]oxazole by known procedures, such as the one described in Chem. Pharm. Bull. 16, 1487 (1968).

Processes for the formation of steroido[3,2-c]pyrazoles (9, 10) are well known. U.S. Pat. No. 3,704,295 discloses a process for the synthesis of 1'-, 2'- or 5'-alkyl substituted 17β-hydroxyandrost-4-en[3,2-c]pyrazoles. U.S. Pat. No. 3,030,358 discloses a process for the reduction of the androst-4-en[3,2-c]pyrazoles to the corresponding 5α-androstan[3,2-c]pyrazoles. An article in Chem. Pharm. Bull. 17, 2319 (1969) reports a process to prepare 5'-aromatic-5α-androstan[3,2-c]pyrazoles. U.S. Pat. No. 3,539,556 discloses a process for the production of 2'-aromatic-17α-ethinylandrost-4-en[3,2-c]pyrazoles. Therefore, procedures are well known to produce steroido[3,2-c]pyrazoles substituted on the pyrazole ring of both the androst-4-en and 5α-androstan series as well as 17α-substituted[3,2-c]pyrazoles. It is highly preferable to transform the 17β-hydroxy group to the desired ether prior to the addition of the [3,2-c]pyrazole ring system.

The 17β-alkoxy[3,2-d]thiazoles (XI) are preferably prepared from the corresponding 17β-hydroxy-5α-androstan-3-one or androst-4-en-3-one by first forming the desired ether at the 17β-position and then forming the [3,2-d]thiazole by known procedures such as the one described in Chem. and Ind. 1625 (1960). The 2α-alkylated-5α-androstano[3,2-d]thiazoles (11) are prepared by the procedure described in Chem. and Ind. 1625 (1960) and Example 39 except that thioacetamide is replaced by the appropriately substituted thioacetamide. For example, if a 2'-benzyl-5α-androstano[3,2-d]thiazole is desired then thioacetamide is replaced by phenylthioacetamide. The thioamide reagents are available or can readily be prepared from the corresponding amide by means well known to those skilled in the art.

The 17β-alkoxy-2-(1-hydroxyalkylidene)-5α-androstan-3-ones (XII) are preferably prepared from the corresponding 17β-hydroxy-5α-androstan-3-one by first forming the desired ether at the 17β-position and then adding the 1-hydroxyalkylidene group at the $C_2$ position by known procedures such as the one disclosed in U.S. Pat. No. 3,135,743. A procedure reported in J. Am. Chem. Soc. 81, 427 (1959) produces 2-hydroxymethylene androstanes. This procedure can also be used starting with other orthoesters, anhydrides or esters other than ethyl formate. With the synthesis of the 2-(1-hydroxyalkylidene)-steroids (XII) the 17β-hydroxyl group must be transformed to the corresponding ether prior to the addition of the substituent at the $C_2$ position because that substituent also contains a hydroxyl group which would also form an ether if the etherification reaction were performed subsequent to the addition of the substituent at the $C_2$ position.

The 17β-alkoxy[2,3-d]imidazoles (XIII) are preferably prepared from the corresponding 17β-hydroxy-5α-androstan-3-one by first forming the desired ether at the 17β-position and then forming the [2,3-d]imidazole by known procedures such as the one described in Chem. Pharm. Bull. 16, 1487 (1968).

The 17β-alkoxy[3,2-d]pyrimidines (XIV) are preferably prepared from the corresponding 17β-hydroxy-5α-androstan-3-one or androst-4-en-3-one by first forming the desired ether at the 17β-position and then forming the [3,2-d]pyrimidine by known procedures such as the one described in U.S. Pat. Nos. 3,026,317 and 3,132,137. U.S. Pat. No. 3,026,317 describes 2'-substituted and U.S. Pat. No. 3,132,137 describes 2'-, 5'-mono- and 2',5'-disubstituted[3,2-d]pyrimidines.

The 2α,3α-epoxides (15) are prepared from the corresponding 5α-androst-2-en by procedures such as the one set forth in U.S. Pat. No. 3,682,898, in particular Example 3. It is preferable to form the desired 17-ether prior to formation of the 2α,3α-epoxide.

Preparations are known for the preparation of the 2α,3α-thioepoxides (15) as well as their 17-methyl, ethyl and THP ethers, see U.S. Pat. No. 3,301,850 in particular Examples 18, 19, and 8, respectively. The 2α,3α-epithio-17-ethers (XV) of the present invention are prepared by analogous procedures. U.S. Pat. No. 3,682,898 also discloses a process to prepare 2α,3α-thioepoxides (15) in general and more specifically 7α-methyl-2α,3α-thioepoxides.

The male contraceptive steroids (I-XV) of the present invention may be used either individually or in combination with each other in the compositions and the methods of treatment of the present invention.

The male contraceptive steroids (I-XV) as well as the compositions and methods of the present invention are used to provide reversible contraception for male mammals post puberty which are selected from the group consisting of man, male dog, tom, bull, stallion, ram, boar, male rat, and male mouse.

With regards to the human, there are many instances in which the female cannot take various types of chemical contraceptive agents and does not wish or cannot use various physical contraceptive devices such as IUD (IUCD) or diaphragm. In addition, many women do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into 2 groups-domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used or even if the particular males are well suited to fertilizing the females it may be desired that they not do so at the present time. The use of the compounds (I-XV), compositions and methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the compounds and methods of the present invention. These rodents can be controlled and/or eradicated by inhibiting the fertility of these rodents by use of the compounds (I-XV), compositions and methods of the present invention. This of course would not eliminate the rodents which are present, but only future rodents which these animals might conceive thereby decreasing future populations of these undesirable animals.

While testosterone and some of its derivatives have been suggested and tried in man as contraceptives in the past, these agents had the distinct disadvantage of typical androgenic side effects which include prostate enlargement, seminal vesicle enlargement, excess and unwanted hair growth and behavioral disturbances. The compounds (I-XV), compositions and methods of treatment of the present invention surprisingly and unexpectedly cause male contraception without causing the typical unwanted androgenic side effects when given in the effective dose range.

The male contraceptive steroids (I-XV) of the present invention are administered such that the male mammal receives about 0.01 to about 15 mg./kg./day. For a 70 kg. male the amount would be about 0.7 mg. to about 1,050 mg./day.

Since the male contraceptive steroids (I-XV) must be in the blood stream daily to be effective they can be administered daily by tablet, capsule, liquid, treat, bait or veterinary premix incorporated into an animal's feed.

The exact dose of the male contraceptive steroid (I-XV) will depend on the particular compound, the weight, age, physical condition and particular patient to be treated.

The male contraceptive steroids (I-XV) are administered in a pharmaceutical compositions of following types: tablets, capsules, liquids (elixirs, syrups, suspensions, emulsions), treats, bait, veterinary premix and animal feed.

Various types of tablets and capsules are known to those skilled in the art for formulating pharmaceutical compositions for use by man.

Types of oral tablets are, for example, compressed (including chewable and lozenge), tablet triturates, enteric-coated, sugar-coated, film-coated, and multiple compressed. Capsules are either hard or soft elastic gelatin.

Pharmaceutically acceptable substances utilized in compressed tablets are binders, lubricants, diluents, disintegrating agents, coloring agents, flavoring agents, flow-inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose high polymer. Multiple compressed tablets are compressed tablets made by more than one compression cycle utilizing the pharmaceutically acceptable substances previously mentioned. Coloring agents are utilized in all the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 thru 000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil and polysorbate 80.

The individual oral solid pharmaceutical dosage forms, tablets and capsules, are packaged individually (unit-dose) or in quantity (multiple-dose containers), for example, bottles of 50, 100, 500, 1000, or 5000. The amount of the male contraceptive steroid per dosage unit (tablet or capsule) is adjusted so that a tablet or capsule, a fraction or multiple thereof, provides the patient with an effective amount. It is preferred that each tablet or capsule contains 1-250 mg. of the male contraceptive steroid (I-XV). The exact dose depends on the particular compound, the age, weight, physical condition and the particular patient or animal as is known in the art. Tablets and capsules are given in sufficient number and frequency to obtain the desired pharmacological effect.

The sustained release tablets and capsules provide an effective amount upon ingestion and continue to release a sufficient amount of the male contraceptive steroid (I-XV) to keep the concentration of the active ingredient at an effective level for increased periods of time, for example, 12-24 hours.

U.S. Pat. No. 3,150,042 discloses a tablet formulation used to treat dogs, cats and rabbits.

Treats for male dogs and toms are somewhat similar to tablets. They are discrete dosage units which carry an effective amount (1-200 mg.) of the male contraceptive steroid (I-XV) for the particular animal to be treated. It must contain some flavoring agent which makes it especially attractive to the animal as is known in the art. There are numerous treats on the market for dogs and cats. If a male contraceptive steroid (I-XV) is incorporated the treat is then a pharmaceutical composition within the scope of the present invention.

Many rodenticides are used in the form of bait. Some refer to this as ration, see U.S. Pat. No. 3,659,022. Bait is similar to treat in that it must be attractice to the male rat or male mouse and carry an effective amount (1-100 mg.) of the male contraceptive steroid (I-XV). Since rats and mice are smaller than dogs and cats bait will have a smaller amount of the male contraceptive steroid (I-XV). Many commercial baits now in use may be used. The male contraceptive steroid (I-XV) may either be added to, or replace the active ingredient in the commercial baits. The formulation of bait is well known, see U.S. Pat. No. 3,655,889.

Liquid dosage forms (1-200 mg./ml.) can be used in many different eays. A human may take a teaspoonful daily which contains an effective amount of the male contraceptive steroid (I-XV). For dogs or cats, the liquid may be mixed with their daily feed. The liquid may be formulated as an elixir, syrup, suspension or emulsion as is well known to those skilled in the art. It is preferred that the liquid by a syrup especially when it is to be added to an animal's feed. For example, Cheque ® (mibolerone), marketed by The Upjohn Company, Kalamazoo, Michigan, is added to the animal's feed.

Oral administration also utilizes a veterinary premix for the commercial and domesticated animals. This is an advantageous way to administer the male contraceptive steroids (I-XV) of the present invention to the animal's daily feed as is well known to those skilled in the art. See U.S. Pat. Nos. 3,150,042; 3,261,687; 3,245,797; and 3,482,023.

The feed carriers for domestic and commercial animals comprise in balanced amounts the essential dietary constituents protein, fat, carbohydrate, minerals, and the like. Premixes, for addition to animal feed, contain ingestible bulking agents or diluents which can be dietary constituents, and the male contraceptive steroids of the present invention in a concentration suited for addition to the animal's feed in amounts calculated on the weight of the animal under treatment.

The animal feed compositions should contain from about 0.0005 to about 0.3% (w/w) of the male contraceptive steroid (I-XV) of the present invention.

The veterinary premixes contain from about 0.05 to about 5% (w/w) of the male contraceptive steroids (I-XV) of the present invention. The veterinary premixes are added to the daily feed rations in amounts calculated to provide the male contraceptive steroids (I-XV) of the present invention in daily dosages of from about 0.01 to about 15 mg./kg.

A dry premix suitable for incorporation into the normal diet of dogs is prepared, for example, from the following types and amounts of ingredients:

|  | Kg. |
|---|---|
| PART I | |
| Male Contraceptive Steroid (I-XV) | 1 |
| Liver protein | 64 |
| Whole liver powder | 60 |
| Fish meal | 200 |
| Terra alba | 24 |
| Dicalcium phosphate | 100 |
| Ferrous gluconate powder | 6½ |
| PART II | |
| Lecithin | 32 |
| Wheat germ oil | 11½ |
| Brewer's yeast | 200 |

The Part I ingredients are mixed well together. The Part II wheat germ oil is mixed with the warmed lecithin and this mixture is added slowly to the brewer's yeast. The Part II mixture is then blended well with the Part I mixture to give the final product. Each 3.5 gms. (approximately 1 teaspoonful) of the final mixture contains 5 mgs. of the active ingredient. The proper amount of this premix to be added to the animal ration can be calculated from the weight of the animal, the required dosage of active ingredient, and the amount of food consumed per day. In Kirk's Index of Treatment in Small-Animal Practice, published in 1951 by The Williams and Wilkins Company, there is a table on page 713 of food requirements in dogs:

TABLE IV

Food maintenance requirements of mature dogs

| Body Weight (Kg.) | Grams of food per animal fresh basis (70 percent moisture) per day |
|---|---|
| 1 | 118 |
| 2 | 195 |
| 3 | 262 |
| 4 | 323 |
| 5 | 380 |
| 6 | 433 |
| 7 | 487 |
| 8 | 537 |
| 9 | 583 |
| 10 | 630 |
| 20 | 1040 |
| 30 | 1410 |
| 40 | 1740 |
| 50 | 2043 |

Another table, Number V, is given on page 712 of the same publication.

TABLE V

The following table of approximate quantities of food per day, for maintenance of an adult animal in a well-nourished condition, is one which is considered fairly reliable as a general guide:

St. Bernards, mastiffs, great danes: 2.5-4.5 lbs.
Collies, retrievers, alsations and similar: 1.5-2.5 lbs.
Greyhounds: 1.8-2.5 lbs.
Airedales, chows, bulldogs, and similar: 0.8-1.5 lbs.
Fox terriers, welsh terriers, scotties, etc.: 8-12 ozs.
Pugs, poms, pekingese: 4-8 ozs.
Cats: 4-8 ozs.

From the above tables the amount of premix to be added daily to the food can be calculated. For example, using Table IV, to the 1740 gms. of food per day for a 40 kg. animal, at a daily dosage of 0.5 mg. of active ingredient per kg. of body weight, 4 teaspoonfuls of food supplement are used.

Another example of a veterinary premix is

| Male Contraceptive Streoid (I-XV) | 300 gm. |
|---|---|
| Soybean meal | 9700 gm. |
| Chloroform, USP | 1500 ml. |
| | 10,000 gm. |

A chloroform solution of the male contraceptive steroid (I-XV) is prepared and incorporated gradually and uniformly into the soybean meal. After adequate mixing the whole is vacuum dried to remove any trace of chloroform.

Each gm. of the premix contains 30 mgs. of the active ingredient. The premix is added to the standard ration of feed.

An equally satisfactory premix is prepared by omitting the chloroform and using mineral oil to facilitate the preparation of a uniform premix which is well suited for later incorporation into the animal ration.

Ready-mixed feed may be prepared in the following manner:

Commercial dog feed: 100 lbs.

Male Contraceptive Steroid (I-XV): 400 mgs.

The male contraceptive steroid (I-XV) is worked into a portion of the feed by careful mixing and the mix is incorporated uniformly into the remaining feed by milling. Each pound of the finished preparation contains 4 mgs. of the steroid (I-XV) providing a total daily dose of 5 mgs. for a 10 kilo dog eating 1¼ lbs. of the feed per day. This daily dose is effective in preventing conception.

The formulation of animal feed and veterinary premix for the remainder of the non-human animals within the scope of the present invention is well within the knowledge of those skilled in the art.

The pharmaceutically therapeutically active compounds (I-XV) are administered orally in unit-dosage forms or multiple-dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include bottles of tablets or capsules (oral-solid) or bottles of pints or gallons (oral-liquid). Hence, multiple dose form is a multiple of unit-doses which are not segregated in packaging. The specifications for the unit-dosage form and the multiple-dosage form are dictated by and directly dependent on (a) the unique characteristics of the therapeutically active compound and the particular therapeutic effect to be achieved and (b) the limitations inherent in the art of compounding such a therapeutically active compound for male contraception.

Regardless of which type of pharmaceutical composition or veterinary premix is used in the methods of treatment of the present invention, a period of pretreatment with the male contraceptive steroid (I-XV) is required. For the male contraceptive steroids (I-XV) of the present invention to exert their contraceptive effect, the male animal should be pretreated continuously for a minimum period of 30-90 days depending on the length of the animal's spermatogenic cycle. Following this pretreatment period the male animal may be safely mated with a female animal of the same species at the time of ovulation or estrus without conception taking place. In order to insure continued contraception after the pretreatment period the male animal must maintain a continuous and relatively uniform blood level of the male contraceptive steroids (I-XV). Therefore, the male animal must continue to take daily doses (tablet, capsule, veterinary premix).

Following cessation of the daily administration of the male contraceptive steroid (I-XV) contraception will be maintained for only a very short period, about 21 days. Gradually over a period of about 90 days the male animal's ability to fertilize the female partner returns to normal.

The definitions and explanations below are for the terms as used throughout the entire patent application including both the specification and claims.

All temperatures are in degrees Centigrade.

TLC refers to thin-layer chromatography.

THF refers to tetrahydrofuran.

DMF refers to dimethylformamide.

SSB refers to an isomeric mixture of hexanes.

p-TSA refers to p-toluenesulfonic acid.

Saline refers to an aqueous saturated sodium chloride solution.

MS refers to mass spectrometry expressed as m/e or mass/charge unit.

IR refers to infrared spectroscopy.

UV refers to ultraviolet spectroscopy.

CD refers to circular dichroism.

CMR refers to C-13 magnetic resonance spectroscopy, chemical shifts are reported in ppm ($\delta$) downfield from TMS.

NMR refers to nuclear (proton) resonance spectroscopy, chemical shifts are reported in ppm ($\delta$) downfield from TMS.

Pharmaceutically acceptable refers to those properties and/or substances which are acceptable to the patient from a pharmacological-toxicological point of view and to the manufacturing pharmaceutical chemist from a physical-chemical point of view regarding compositions, formulation, stability, patient acceptance and bioavailability.

When solvent pairs are used, the ratio of solvents used are volume/volume (v/v).

$R_2$ is a hydrogen atom or methyl group.

$R_{2a}$ is a hydrogen atom, alkyl of 1 thru 4 carbon atoms or benzyl.

$R_{2\beta}$ is a hydrogen atom or methyl group with the proviso that when $R_{2\beta}$ is methyl, $R_{2\alpha}$ is also methyl.

$R_{2a}$ is alkyl of 1 thru 3 carbon atoms, or

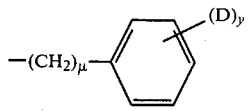

$R_{2b}$ is $R_{2a}$, —SH, —SCH$_3$ or amino.
$R_3$ is alkyl of 1 thru 4 carbon atoms or phenyl.
$R_4$ is $R_{2a}$ or phenyl.
$R_6$ is a hydrogen atom or methyl group.
$R_7$ is a hydrogen atom or methyl group.
$R_{17\alpha}$ is a hydrogen atom, alkyl of 1 thru 4 carbon atoms, alkenyl of 2 thru 4 carbon atoms or alkynyl of 2 thru 4 carbon atoms.
$R_{17\beta}$ is alkyl of 1 thru 16 carbon atoms,

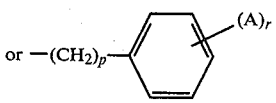

—(CH$_2$)$_n$—CH(CH$_2$)$_m$, —CH$_2$—alkenyl where alkenyl is 2 thru 15 carbon atoms or —CH$_2$—C≡CH, $R_{17\alpha}$ and $R_{17\beta}$ can be connected to form a cyclic ether containing 4 or 5 carbon atoms. A is a methyl, methoxy, trifluoromethyl, hydroxyl or nitro group or a hydrogen, fluorine, chlorine or bromine atom.

D is a methyl, methoxy, trifluoromethyl, hydroxyl or nitro group or a hydrogen, fluorine, chlorine or bromine atom.

M is a methyl, methoxy, trifluoromethyl, hydroxyl or nitro group or a hydrogen, fluorine, chlorine or bromine atom.

Q is an oxygen or sulfur atom.
X is a fluroine, chlorine or bromine atom.
Z is a hydrogen atom, alkyl of 1 thru 4 carbon atoms or —(CH$_2$)$_p$— [phenyl with (A)$_r$], that for compounds of formula (XIV) the Z's may be the same or different.
m is 4 thru 6.
n is 0 thru 4.
p is 0 thru 4.
q is 1 or 2 when q is 2, the M's can be the same or different.
y is 1 or 2, when y is 2, the D's can be the same or different.
R is 1 or 2, when r is 2, the A's can be the same or different.
μ is 0 thru 4.
~ indicates the attached group can be in either the α or β configuration.
-- indicates the bond can be a single or double bond.
[2,3-d]oxazole (8, VIII) refers to

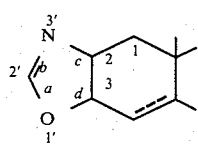

[3,2-c]pyrazole (9, IX) refers to

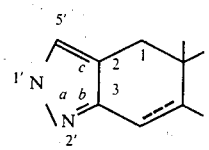

[3,2-c]pyrazole (10, X) refers to

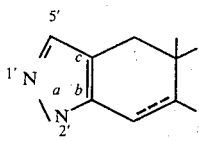

[3,2-d]thiazole (11, XI) refers to

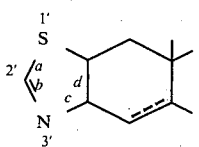

[3,2-d]pyrimidine (14, XIV) refers to

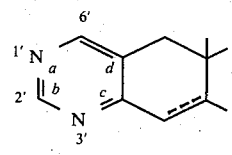

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

Preparation 1

2-Ethylidene-17β-methoxy-5α-androstan-3-one

A mixture of 17β-methoxy-5α-androstan-3-one (U.S. Pat. No. 3,301,850, Example 14, 8 g.), potassium hydroxide (2.1 g.) and acetaldehyde (5 ml.) in absolute ethanol (500 ml.) is stirred for 16 hours under nitrogen. The potassium hydroxide is then neutralized with acetic acid and the mixture concentrated to about 100 ml. Water is added and the product is extracted with diethyl ether. After the diethyl ether is removed the steroid is chromatographed over silica gel and then alumina. The appropriate fractions are pooled and concentrated to give both isomers of the product, IR (neat) 1720 and 1690 cm$^{-1}$; MS (m/e) 330; NMR (CDCl$_3$) 0.79, 0.78, 0.83, 1.72, 3.22, 3.35 and 6.75 δ; and UV (ethanol) λ=246 nm (ε=4,300).

EXAMPLE 1

17β-Benzyloxy-5α-androstan-3-one (I)

A mixture of 17β-hydroxy-5α-androstan-3-one 3-ethylene ketal (1.0 g.), benzyl chloride (10 ml.), sodium hydroxide (50%, 5 ml.), and tetrabutylammonium bisulfate (100 mg.) are stirred at 20°–25° for 24 hrs., an additional 100 mg. of tetrabutylammonium bisulfate is added and the mixture stirred an additional 16 hours. The 17-ether is obtained by extraction. Water is added to the crude product and removed under reduced pressure to codistill some oily by-products. The residue is triturated with SSB to give crystalline benzyl ether 3-ketal. The ketal is dissolved in acetone (20 ml.) and perchloric acid (1.0 N, 0.2 ml.) and refluxed 1 hour. A stream of nitrogen is used to remove some of the acetone. Water is added to precipitate the product. After recrystallization from SSB the title compound is obtained, m.p. 126°–128°; MS (m/e) 380, 290, 271 and 91; IR (mull) 1610 and 1495 cm$^{-1}$; NMR (CDCl$_3$) 0.84, 1.01, 3.43, 4.53 and 7.31 δ.

EXAMPLE 2

17β-Hexadecanoxy-5α-androstan-3-one (I)

A mixture of 17β-hydroxy-5α-androstan-3-one 3-ethylene ketal (1.0 g.), 1-chlorohexadecane (20 ml.), sodium hydroxide (50%, 10 ml.) and tetrabutylammonium bisulfate (200 mg.) is stirred at 20°–25° for 3 days. The 17-ether is obtained by extraction. The 3-ketal is hydrolyzed by refluxing with perchloric acid for 1 hour. The crude product is column chromatographed twice over silica gel eluting with a gradient of SSB (5 l.) and SSB:ethyl acetate (80:20, 5 l.). The appropriate fractions (TLC) are pooled and concentrated to give the title compound which is recrystallized from acetone, m.p. softens at 70° and flows at 77°; IR (mull) 1720 and 720 cm$^{-1}$; MS (m/e) 486 and 272; NMR (CDCl$_3$) 0.76, 1.01, 1.25 and 3.34 δ.

EXAMPLE 3

17β-n-Heptanoxy-5α-androstan-3-one (I)

Following the general procedure of Examples 1 and 2 and making non-critical variations but starting with 1-chloroheptane as the alkyl halide, the title compound is obtained, MS (m/e) 388, 373, 277 and 257; IR (mull) 1720, 1145, 1115 and 1100 cm$^{-1}$.

EXAMPLE 4

17β-(2-Propenyloxy)-5α-androstan-3-one (I)

Following the general procedure of Examples 1 and 2 and making non-critical variations but starting with 3-chloropropene as the alkyl halide, the title compound is obtained, m.p. 122°–124°; MS (m/e) 330, 315, 273 and 257; IR (mull) 1715 and 1650 cm$^{-1}$; NMR (CDCl$_3$) 0.79, 0.94, 3,34, 3,98, 5.2 and 5.85 δ.

EXAMPLE 5

17α-Ethinyl-17β-(2-propenyloxy)-5α-androstan-3-one (I)

Step A—17α-Ethinyl-17β-hydroxy-5α-androstan-3-one 3-ethylene ketal

Following the general procedure of Example 12, Step A, and making non-critical variations but starting with 17β-hydroxy-5α-androstan-3-one instead of 17β-hydroxy-2α-methyl-5α-androstan-3-one, 17α-ethinyl-17β-hydroxy-5α-androstan-3-one 3-ethylene ketal is obtained, recrystallized from THF-SSB, m.p. 269°–274°; NMR (CDCl$_3$) 0.83, 2.55 and 3.92 δ.

Step B—17α-Ethinyl-17β-(2-propenyloxy)-5α-androstan-3-one 3-ethylene ketal

Sodium hydroxide (50%, 10 ml.) and tetrabutylammonium bisulfate) (0.4 g.) is added to the ketal (Step A, 1.0 g.) in 3-chloropropene (40 ml.). The mixture is stirred (2 hours) following which diethyl ether and water are added. The organic phase is separated, washed to neutrality, dried over magnesium sulfate and concentrated to give 17α-ethinyl-17β-(2-propenyloxy)-5α-androstan-3-one 3-ethylene ketal.

Step C

The ketal group is hydrolyzed using dilute hydrochloric acid in acetone. The product is purified by column chromatography over silica gel eluting by gradient between ethyl acetate:SSB (5:95, 5 l.) and ethyl acetate:SSB (30:70, 5 l.). The appropriate fractions (TLC) are pooled and concentrated to give the title compound, recrystallized from aqueous acetone, m.p. 119°–125°; MS (m/e) 354 and 349; NMR (CDCl$_3$) 0.88, 1.01, 2.57, 4.00, 4.12, 4.15, 4.33 and 6.3δ.

EXAMPLE 6

17α-Ethinyl-17β-methoxy-5α-androstan-3-one (I)

Step A—17α-Ethinyl-17β-hydroxy-5α-androstan-3-one 3-ethylene ketal

See Example 5, Step A.

Step B—17α-Ethinyl-17β-methoxy-5α-androstan-3-one 3-ethylene ketal

A slurry of the ketal (Step A, 1.79 g.) and toluene (50 ml.) is concentrated to dryness with warming on a rotary evaporator to remove traces of water. The residue is again slurried with toluene (50 ml.) and thallous ethoxide (0.4 ml.) is added. The mixture is warmed to about 40° and the toluene removed on the rotary evaporator. Toluene (50 ml.) is again added, the mixture warmed to 40°, and the toluene removed as before. Acetonitrile (50 ml.), toluene (20 ml.) and methyl iodide (5 ml.) are added. The mixture is stirred and refluxed gently for about 5 hours. The mixture is filtered thru a bed of Celite. The filtrate is taken up in diethyl ether and filtered again to remove insoluble matter. The diethyl ether is removed and the steroid material is column chromatographed over silica gel eluting by gradient between ethyl acetate:SSB (5:95, 5 l.) and ethyl acetate:SSB (30:70, 5 l.). The appropriate fractions (TLC) are pooled and concentrated to give 17α-ethinyl-17β-methoxy-5α-androstan-3-one 3-ethylene ketal, NMR (CDCl$_3$) 0.81, 2.58, 3.37, and 3.91δ.

Step C—17α-Ethinyl-17β-methoxy-5α-androstan-3-one (I)

The ketal (Step B) is dissolved in acetone (15 ml.) and hydrochloric acid (4 N, 2 ml.) is added. After a few hours, water is added and the precipitate filtered, washed with water, dried and recrystallized from acetone-water to give the title compound, m.p. 198°–201°; NMR (CDCl$_3$) 0.86, 1.01, 2.57 and 3.38 δ; MS (m/e) 328, 299, 281 and 231.

EXAMPLE 7

17α-Ethyl-17β-methoxy-5α-androstan-3-one (I)

Step A—17α-Ethyl-17β-hydroxy-5α-androstan-3-one

A mixture of 17α-ethinyl-17β-hydroxyandrost-4-en-3-one (5 g.) and palladium on calcium carbonate (3%) in ethanol (95%, 300 ml.) is shaken under hydrogen pressure for 1.5 hours. The catalyst is removed by filtration and the filtrate concentrated to a residue which is chromatographed over a silica gel column (300 g.) eluting by gradient between ethyl acetate:SSB (5:95, 5 l.) and ethyl acetate:SSB (30:70, 5 l.). Appropriate fractions (TLC) are pooled and concentrated. The steroid material is recrystallized twice from diethyl ether and then from isopropyl ether to give the title compound, m.p. 148°–150°; IR (mull) 1715; NMR (CDCl$_3$) 0.89, 0.95 and 1.02; CD (dioxane) λ=295 nm (θ= +3500).

Step B—17α-Ethyl-17β-methoxy-5α-androstan-3-one

Following the general procedure of Example 8 and making non-critical variations but starting with 17α-ethyl-17β-hydroxy-5α-androstan-3-one (Step A) the title compound is obtained. If desired, chromatography may be used for purification.

EXAMPLE 8

17β-Methoxy-17α-methyl-5α-androstan-3-one (I)

Step A—17β-Hydroxy-17α-methyl-5α-androstan-3-one 3-ethylene ketal

Ethylene glycol (20 ml.) and p-TSA (5 mg.) is added to 17β-hydroxy-17α-methyl-5α-androstan-3-one (3.0 g.) in methylene chloride (20 ml.). The mixture is heated on a steam bath until most of the methylene chloride is removed. The remainder of the methylene chloride is removed on a rotary evaporator. The mixture is cooled and a small amount of a sodium bicarbonate solution and water are added and the mixture filtered. The filtered solids are washed and dried to give the subtitle compound, NMR (CDCl$_3$), 0.83, 0.84, 1.20 and 3.92 δ.

Step B—17β-Methoxy-17α-methyl-5α-androstan-3-one 3-ethylene ketal

A mixture of 17β-hydroxy-17α-methyl-5α-androstan-3-one 3-ethylene ketal (Step A, 2.0 g.), silver oxide (2.4 g.), methyl iodide (2.4 ml.) and diisopropylethyl amine (3.4 ml.) and DMF (20 ml.) is stirred at 5° for 2 days. Diethyl ether is added and the mixture filtered to remove the inorganic precipitate. The precipitate is washed with diethyl ether and the filtrates combined and successively washed with water, dilute hydrochloric acid, water, dilute sodium bicarbonate solution and water. The organic phase is dried over magnesium sulfate and concentrated to give a residue. The residue is recycled thru the same reaction conditions and work-up. The crude product is column chromatographed over silica gel by gradient elution between ethyl acetate:SSB (5:95) and ethyl acetate:SSB (25:75). The appropriate fractions (TLC) are pooled and concentrated to give the ketal, NMR (CDCl$_3$) 0.82, 0.84, 1.18, 3.22 and 3.92 δ.

Step C—17β-Methoxy-17α-methyl-5α-androstan-3-one (I)

The ketal (Step B) is dissolved in acetone (15 ml.) and hydrochloric acid (2 N, 2 ml.). The reaction mixture is heated briefly and after 2 hours TLC shows the ketal has been removed. The product is precipitated by the addition of water. The precipitate is recovered by filtration, washed and recrystallized from aqueous acetone to give the title compound, m.p. 130°–131°; MS (m/e) 318, 303, 286, 271 and 244; NMR (CDCl$_3$) 0.87, 1.02, 1.19 and 3.23 δ.

EXAMPLE 9

17α-Methyl-17β-(2-propenyloxy)-5α-androstan-3-one (I)

A mixture of 17β-hydroxy-17α-methyl-5α-androstan-3-one 3-ethylene ketal (Example 8, 1.0 gm.), tetrabutylammonium bisulfate (0.4 gm.) aqueous sodium hydroxide (50%, 5 ml.) and 3-chloropropene (30 ml.) is stirred at 20°–25° for 2 days. The reaction mixture is then diluted with diethyl ether and washed well with water and concentrated to a crystalline residue. The crystalline residue is recycled using the same amount of reagents and the same type of work up. The crude product is column chromatographed over silica gel. The appropriate fractions are pooled and concentrated to give a partially oily product, which is heated briefly in acetone (15 ml.) containing hydrochloric acid (2 N, 2 ml.) to remove the ketal group. The desired product is extracted with diethyl ether and the ether extract washed and then concentrated and column chromatographed over silica gel. The appropriate fractions are pooled and concentrated to give a residue which is recrystallized from acetone-water to give the title compound, m.p. 115°–117°; MS (m/e) 344, 339, 286, 271, and 244; NMR (CDCl$_3$) 0.90, 1.02, 1.21, 3.90, 7.54, 7.81 and 8.3 δ.

EXAMPLE 10

4′,5′-Dihydrospiro[5α-androstan-17,2′(3′H)-furan]-3-one (I)

Lithium wire (10 gm.) cut into small pieces is added under nitrogen to a mixture of 5α-androstan-3,17-dione 3-ethylene ketal (4.5 gm.) prepared according to Jones, et al., J. Chem. Soc., Perkins I 1356-9 (1975) in THF (120 ml.). The mixture is stirred rapidly with sufficient cooling to maintain a temperature of 5°–15°. 1-Chloro-3-dimethylaminopropane (8 ml.) is added dropwise over a half hour period. The temperature is kept at 10°–12° for another half hour and then two additional portions (10 ml. each) of the chloroamine base are added under nitrogen at intervals of 25 minutes. After two and one-half hours the unreacted lithium is filtered and the reaction mixture diluted with ice and water. The product is extracted with ethyl acetate. The organic phase is dried over sodium sulfate and the organic diluent is removed by reduced pressure. The product is purified by trituration with a mixture of hexanes and diethyl ether and recrystallized from aqueous acetone. The crude product is mixed with methyl iodide (7 ml.) and methanol (42 ml.) to give the quaternary iodide. This salt is dissolved in methanol (50 ml.) and one equivalent of sodium hydroxide and water (50 ml.) are added. The mixture is heated at 100° then ethylene glycol (100 ml.) is added and the mixture distilled until the temperature reaches 185°. After 6 hours at this temperature the reaction mixture is cooled and diluted with water to precipitate the product. The product is purified by column chromatography over silica gel. The appropriate fractions (TLC) are pooled and concentrated to yield the product which is crystallized if necessary. The 3-ketal is removed by dissolving the product in acetone (20 ml.)

and hydrochloric acid (2 N, 2 ml.); after warming for a few minutes, the product is precipitated by the addition of water. The product is collected by filtration and recrystallized from acetone-hexane to give the title compound.

EXAMPLE 11

17β-Benzyloxy-2α-methyl-5α-androstan-3-one (I)

A mixture of 17β-hydroxy-2α-methyl-5α-androstan-3-one (J. Am. Chem. Soc. 81, 427 (1959, 0.5 g.), methylene chloride (4 ml.), ethylene glycol (4 ml.) and p-TSA (few crystals) is boiled on a steam bath. After most of the methylene chloride boils off the mixture is further concentrated by reduced pressure and heating on a steam bath. The mixture is cooled, diluted with sodium bicarbonate solution and water. The 3-ketal is collected by filtration, washed well with water and dried under reduced pressure.

Following the general procedure of Example 1 but starting with 17β-hydroxy-2α-methyl-5α-androstan-3-one 3-ethylene ketal instead of 17β-hydroxy-5α-androstan-3-one 3-ethylene ketal the title compound is obtained, m.p. 116°–120°; IR (mull) 1715, 1605, 1585, and 1495 cm$^{-1}$; MS (m/e) 394, 304, 285 and 91; NMR (CDCl$_3$) 0.84, 1.06, 1.99, 3.40, 4.53 and 7.30 δ.

EXAMPLE 12

17α-Ethinyl-17β-methoxy-2α-methyl-5α-androstan-3-one (I)

Step A—17α-Ethinyl-17β-hydroxy-2α-methyl-5α-androstan-3-one 3-ethylene ketal

A mixture of 17β-hydroxy-2α-methyl-5α-androstan-3-one (J. Am. Chem. Soc. 81, 427 (1959), 3.83 g.), chloroform (7 ml.), p-TSA (0.17 g.) and ethylene glycol (29 ml.) is heated on a steam bath for 10 minutes. The mixture is then transferred to a rotary evaporator and the heating is continued for a few minutes. The mixture is then diluted with dilute sodium bicarbonate, the precipitate filtered, washed and dried to give the 3-ketal.

The crude 3-ketal is dissolved in methylene chloride (43 ml.) and sodium acetate (3.6 g.) and cooled in an ice bath. Pyridinium chlorochromate (9.3 g.) is added. After 1 hour the reaction mixture is washed with water and sodium bicarbonate solution, dried over sodium sulfate, concentrated and recrystallized from acetone-SSB to give 2α-methyl-5α-androstane-3,17-dione 3-ethylene ketal.

The ketone is dissolved in THF (purified by percolating thru alumina, 37 ml.) and potassium t-butoxide (20% in THF, 8.85 ml.) is added. Acetylene is bubbled thru for 15 minutes. The reaction is monitored by TLC (alumina plates developed with ethyl acetate-hexane, 30:70). Saline is added, the THF phase separated and washed with saline, dried, concentrated and recrystallized from THF-SSB to give 17α-ethinyl-17β-hydroxy-2α-methyl-5α-androstan-3-one 3-ethylene ketal, m.p. 253°–257°; NMR (CDCl$_3$) 0.83, 2.55 and 3.92 δ.

Step B—17α-Ethinyl-17β-methoxy-2α-methyl-5α-androstan-3-one (I)

Following the general procedure of Example 6, Step C and making non-critical variations but starting with the 2α-methyl compound of Step A, the title compound is obtained, recrystallized from acetone-SSB, m.p. 166°–170°; NMR (CDCl$_3$) 0.86, 1.00, 1.07, 2.57 and 3.38 δ; MS (m/e) 342, 327, 313, 295 and 245.

EXAMPLE 13

2α-Ethyl-17β-methoxy-5α-androstan-3-one (I)

Step A—2β-Ethyl-17β-methoxy-5α-androstan-3-one

Palladium on charcoal (5%, 110 mg.) is added to a solution of 2-ethylidene-17β-methoxy-5α-androstan-3-one (Preparation 1, 1.5 g.) and shaken under hydrogen. The catalyst is removed by filtration and the filtrate is concentrated to dryness and chromatographed to give 2β-ethyl-17β-methoxy-5α-androstan-3-one.

Step B—2α-Ethyl-17β-methoxy-5α-androstan-3-one (I)

2β-Ethyl-17β-methoxy-5α-androstan-3-one (Step A) is dissolved in ethanol (95%, 13 ml.) followed by addition of sodium hydroxide (50%, 14 drops). After stirring at 20°–25° for 4.5 hrs. the mixture is extracted with diethyl ether, the diethyl ether extract is concentrated under reduced pressure to yield the title compound, which is recrystallized twice from methanol; m.p. 105°–107°; NMR (CDCl$_3$) 0.77, 1.05, 3.20 and 3.33 δ.

EXAMPLE 14

17β-Methoxy-2,2-dimethyl-5α-androstan-3-one (I)

17β-Hydroxy-5α-androstan-3-one (50 g.) in DMF (500 ml.) is cooled to 5° in an ice bath and silver oxide (58 g.) and N,N-diisopropylethylamine is added (85 ml.). The mixture is stirred and methyl iodide (142 g.) is slowly added keeping the temperature at about 5°. The stirring is continued and the mixture is allowed to come to 20°–25°. After 17 hours diethyl ether (2 l.) is added and the mixture filtered thru a bed of Celite to remove the inorganic solids. The filtrate is washed with water, dilute hydrochloric acid, water again, and dried over sodium sulfate, then filtered, and concentrated. The concentrate is column chromatographed over silica gel. The appropriate fractions (TLC) are pooled and concentrated to give the title compound, m.p. 116°–120°, IR (mull) 1700 cm$^{-1}$; NMR (CDCl$_3$) 0.77, 1.01, 1.08, 1.18, 3.24, and 3.37 δ.

EXAMPLE 15

17β-Methoxy-2α-methyl-5α-androstan-3-one oxime (I)

A mixture of 17β-methoxy-2α-methyl-5α-androstan-3-one (Acta. Endocrinology 36, 83 (1961), 0.5 g.), hydroxylamine hydrochloride (0.218 g.) and sodium acetate (0.258 g.) in ethanol (20 ml.) is refluxed for 1 hour. Water is then added; a precipitate forms which is filtered, washed, dried and recrystallized from methylene chloride-acetone to give the title compound, m.p. 203°–211°; IR (mull) 3360 and 1650 cm$^{-1}$; MS (me) 333; NMR (CDCl$_3$) 0.75, 0.93, 1.06, 3.15 and 3.33 δ.

EXAMPLE 16

17β-Methoxy-7β-methylandrost-4-en-3-one (I) and 17β-methoxy-2α,7β-dimethylandrost-4-en-3-one (I)

A mixture of 7β-methyltestosterone (U.S. Pat. No. 3,341,557, Example 7, 5 g.), DMF (50 ml.), methyl iodide (6.4 ml.), diisopropylethylamine (9 ml.) and silver oxide (6 g.) are stirred together with cooling in an ice bath. The mixture is stirred continually as the ice is allowed to melt. The mixture is stirred overnight, diluted with diethyl ether and filtered. The filtrate is washed with water, dilute hydrochloric acid, dilute sodium bicarbonate, dried and concentrated to an oily residue. The oily residue is column chromatographed over silica gel (250 g.) eluting by gradient between SSB (5 l.) and SSB:ethyl acetate (75:25, 5 l.). A first series of homogeneous one-spot (TLC) fractions are pooled and concentrated to a solid which upon recrystallization gives 17β-methoxy-2α,7β-dimethylandrost-4-en-3-one (I), m.p. 123°–126°; UV (ethanol) λ=244 nm (ε=15,150); IR (mull) 1670, 1660, 1625 and 1115 cm$^{-1}$; MS (m/e) 330, 315, 289, 274 and 161.

A second series of oily fractions are pooled, concentrated and rechromatographed to give 17β-methoxy-7β-methylandrost-4-en-3-one (I), UV (ethanol) λ=242 nm (ε=16,550); IR (mull) 1680, 1620 and 1120 cm$^{-1}$; MS (m/e) 316, 301, 274 and 242.

EXAMPLE 17

17α-Ethinyl-17β-methoxyandrost-4-en-3-one (I)

Thallous ethoxide (0.8 ml.) is added to ethisterone (17α-ethinyl-17β-hydroxyandrost-4-en-3-one, 3.44 g.) in benzene (50 ml.). After mixing, the benzene is removed with the rotary evaporator and acetonitrile (50 ml.), benzene (40 ml.) and methyl iodide (1.7 ml.) are added. The mixture is refluxed and stirred for 2 hours. Additional methyl iodide (2 ml.) is added and the mixture refluxed another 2 hours. The precipitated thallous iodide is filtered off and the filtrate is concentrated to a residue which is taken up in boiling SSB and filtered thru Celite. After concentration the product is column chromatographed over silica gel eluting with increasing amounts of ethyl acetate in SSB. The appropriate fractions (TLC) are pooled and concentrated to give the title compound (recrystallized from SSB): m.p. 127°–131°; UV (ethanol) λ=240 nm (ε=16,500); MS (m/e) 326 and 311; IR (mull) 3240, 2100, 1670 and 1620 cm$^{-1}$.

EXAMPLE 18

17β-Methoxy-2α-methylandrost-4-en-3-one (I)

Testosterone (50 g.) in DMF (500 ml.) is cooled to 5° in an ice bath and silver oxide (58 g.) and N,N-diisopropylethylamine (85 ml.) are added. The mixture is stirred and methyl iodide (142 g., 62 ml.) is added in a slow stream. The temperature remains about 5° initially, the stirring is continued without further addition of ice to the bath and the mixture comes to 20°–25°. After 18 hours, diethyl ether (2 l.) is added and the mixture is filtered thru a bed of celite. The filtrate is washed successively with water, dilute hydrochloric acid, again with water, dried over sodium sulfate, filtered and concentrated. The concentrate is column chromatographed over silica gel (1 kg.) eluting by a gradient between SSB (5 l.) and SSB-ethyl acetate (80:20, 5 l.). The appropriate fractions (TLC) are pooled and concentrated to give the title compound; m.p. 130°–145°; UV (ethanol) λ=240 nm (ε=15,000); IR (mull) 1670 cm$^{-1}$; NMR (CDCl$_3$) 0.8, 1.1, 1.21, 3.26, 3.32, and 5.71 δ; MS (m/e) 316.

EXAMPLE 19

17β-Methoxy-2α-methylandrost-4-en-3-one (I)

Step A—17β-Hydroxy-2α-methylandrost-4-en-3-one

17β-Hydroxyandrost-4-en-3-one (4.95 g.) is dissolved in diethyl ether (110 ml.) with stirring under nitrogen. Sodium methoxide (1.18 g.) is added. Diethyloxalate (3.46 ml.) in diethyl ether (26 ml.) is added over a period of 15 minutes and the mixture stirred at 20°–25° for five hours. The solid material is collected on a filter and washed with diethyl ether and petroleum ether. The solid material is dried under reduced pressure at 20°–25°.

The solid material (2.0 g.) is dissolved in water (20 ml.) and acidified to pH 3. The precipitate which comes out of solution is collected on a filter, washed with a small amount of water, and dried under reduced pressure. This residue, potassium carbonate (11.0 g.), methyl iodide (11 ml.) and acetone (90 ml.) are heated overnight at reflux. After reflux the mixture is allowed to cool and filtered to remove the solids. The solids are washed once with acetone. The filtrates are combined and concentrated to give a gummy residue.

The gummy residue is dissolved in methanol (45 ml.), sodium methoxide (3.7 ml.) is added and the mixture is allowed to stand at 20°–25° for 2 hours and then cooled to 4°. The mixture is then diluted with cold water and extracted 3 times with diethyl ether:methylene chloride (2:1). The organic mixture is then washed 3 times with water and once with saline. The aqueous washes are backwashed with diethyl ether. The organic fractions are pooled, filtered through sodium sulfate and concentrated to give a gummy residue. The gummy residue is column chromatographed over silica gel (400 g.) and eluted with ethyl acetate:cyclohexane (25:75). The appropriate fractions (TLC) are combined, pooled and concentrated to give 17β-hydroxy-2α-methylandrost-4-en-3-one which is crystallized from acetone-SSB.

Step B—17β-Methoxy-2α-methylandrost-4-en-3-one (I)

Following the general procedure of Example 16 and making non-crictial variations but starting with 17β-hydroxy-2α-methylandrost-4-en-3-one (Step A) the title compound is obtained.

EXAMPLE 20

17β-Methoxy-2-spirocyclopropyl-5α-androstan-3-one (II)

Sodium methoxide in methanol (25%, 16.5 ml.) is added to a solution of 17β-methoxy-5α-androstan-3-one (4.0 g.) in t-butyl alcohol (40 ml.) and diethyl oxalate (15 ml.) with stirring under nitrogen. After 1.5 hours diethyl ether and water are added and the mixture acidified with dilute hydrochloric acid. The organic layer is separated, washed with water and made alkaline with sodium hydroxide (1 N). The sodium hydroxide extract containing the glyoxalate is acidified and extracted with diethyl ether. The diethyl ether extract is washed with water, dried over magnesium sulfate and then concentrated under reduced pressure to give the glyoxalate.

The glyoxalate is dissolved in diethyl ether (80 ml.) and cooled in an ice bath, following which lithium hydride in mineral oil (50%, 0.8 g.) is added. Paraformaldehyde is pyrolyzed and the resulting formaldehyde vapors are swept into the diethyl ether mixture during about 20 minutes. After about 1 hour a saturated solution of sodium bicarbonate is added dropwise. The diethyl ether phase is separated, washed with water, dried and filtered thru a short bed of silica gel. The filtrate is concentrated under reduced pressure to give 17β-methoxy-2-methylene-5α-androstan-3-one which is dissolved in diethyl ether (200 ml.) containing an ethereal solution of diazomethane (prepared from 5 g. of N-methyl-N'-nitro-N-nitrosoguanidine). The diazomethane mixture is kept at 20°–25° for 16 hours and then concentrated under reduced pressure. The concentrate is heated under reduced pressure at 140° in a Woods metal bath until the bubbling ceases and is then cooled. The mixture is column chromatographed over two Merck prepacked silica gel columns (size B) eluting with ethyl acetate-hexane (15:85). The appropriate fractions (TLC) are pooled and concentrated to give the title compound, m.p. 117°–122°; MS (m/e) 330, 315, 298, 283, 257; IR (mull) 3080, 1690, 1150 and 1105 cm$^{-1}$; NMR (CDCl$_3$) 0.76, 1.01, 3.20 and 3.33.

EXAMPLE 21

17β-Methoxy-2-spirocyclopropyl-5α-androstan-3-one (II)

Step A—17β-Hydroxy-2-spirocyclopropyl-5α-androstan-3-one

Following the general procedure of Example 20 and making non-critical variations but starting with 17β-hydroxy-5α-androstan-3-one, 17β-hydroxy-2-spirocyclopropyl-5α-androstan-3-one is obtained, m.p. 115°–124°; MS (m/e) 316, 257, 201 and 189; IR (mull) 3300 and 1690 cm$^{-1}$; NMR (CDCl$_3$) 0.5–0.7, 0.80, 1.01 and 3.63 δ.

Step B—17β-Methoxy-2-spirocyclopropyl-5α-androstan 3-one (II)

Following the general procedure of Example 17 and making non-critical variations but starting with 17β-hydroxy-2-spirocyclopropyl-5α-androstan-3-one (Step A) the title compound is obtained.

EXAMPLE 22

17β-Methoxy-1α,2α-methylene-5α-androstan-3-one (III)

Ethereal diazomethane (40 ml. generated from 3 g. of N-methyl-N'-nitro-N-nitrosoguinidine) is added to a mixture of 17β-methoxy-5α-androst-1-en-3-one (IV, Example 23, 1.0 g.) and palladium diacetate (10 mg.) in diethyl ether (20 ml.). After a few hours the organic diluents are removed by reduced pressure and the residue is column chromatographed thru silica gel (100 g.) eluting by gradient between ethyl acetate:SSB (5:95, 5 l.) and ethyl acetate:SSB (20:80, 5 l.). The appropriate fractions (TLC) are pooled and concentrated to give the title compound, m.p. 114°–118°; MS (m/e) 316, 301, 269, and 243; NMR (CDCl$_3$) 0.77, 0.97, 3.23 and 3.34 δ; CMR (CDCl$_3$) 9.66 δ.

EXAMPLE 23

17β-Methoxy-5α-androst-1-en-3-one (IV)

A mixture of 2α-bromo-17β-methoxy-5α-androstan-3-one (U.S. Pat. No. 3,301,850, Example 15, 3.0 g.), lithium carbonate (1.5 g.) and lithium chloride (0.5 g.) in DMF (30 ml.) are heated at reflux under nitrogen for 1.5 hours. The mixture is cooled, filtered and the solids washed with DMF. The filtrate and washings are combined and diluted with water (10 ml.) to give a precipitate. The precipitate is collected, washed, dried and column chromatographed over silica gel (200 g.) eluting by gradient between SSB (5 l.) and SSB:ethyl acetate (70:30, 5 l.). The appropriate fractions (TLC) are pooled and concentrated to give a solid which after recrystallization from hexane gives the title compound, m.p. 115°–117°, UV (ethanol) λ=229 nm (ε=10,350); MS (m/e) 302, 287 and 260; NMR (CDCl$_3$) 0.79, 1.01, 3.20, 3.34, 5.84 and 7.13 δ.

EXAMPLE 24

17β-Methoxy-2-methylandrost-1-en-3-one (IV)

Following the general procedure of Example 8, Steps A, B and C, and making non-critical variations but substituting 17β-hydroxy-2-methylandrost-1-en-3-one [J. Am. Chem. Soc. 82, 5494 (1960)] for 17β-hydroxy-17α-methyl-5α-androstan-3-one the title compound is obtained.

EXAMPLE 25

17β-Methoxy-5α-androstan-2-one (V)

Step A—17β-Hydroxy-5α-androstan-2-one 2-ethylene ketal

Following the general procedure of Example 8, Step A and making non-critical variations but starting with 17β-hydroxy-5α-androstan-2-one (U.S. Pat. No. 3,415,816), 17β-hydroxy-5α-androstan-2-one 2-ethylene ketal is obtained.

Step B—17β-Methoxy-5α-androstan-2-one (V)

Following the general procedure of Example 8, Steps B and C, and making non-critical variations but substituting 17β-hydroxy-5α-androstan-2-one 2-ethylene ketal (Step A) for 17β-hydroxy-17α-methyl-5α-androstan-3-one 3-ethylene ketal the title compound is obtained.

EXAMPLE 26

2α-Chloro-17β-methoxy-5α-androstan-3-one (VI)

Chlorine in acetic acid (0.84 M, 12 ml.) is added dropwise with stirring to 17β-methoxy-5α-androstan-3-one (3.0 g.) in acetic acid (10 ml.). When the addition is complete the reaction mixture is chilled, and the precipitate which forms is filtered off, washed with water, dried and recrystallized from acetone-methylene chloride to give the title compound, m.p. 202°–210°; MS (m/e) 338, 306, 302, 291 and 265; NMR (CDCl$_3$) 0.77, 1.10, 3.20, 3.30 and 4.06 δ.

EXAMPLE 27

3α-Hydroxy-17β-methoxy-5α-androstane and 3β-hydroxy-17β-methoxy-5α-androstane

Sodium borohydride (0.37 gms.) is added to a mixture of 17β-methoxy-5α-androstan-3-one (3 gms.) and isopropylalcohol (95%, 35 ml.). The mixture is stirred at 20°–25° for one hour and then is concentrated to dryness. The residue is column chromatographed on a size C prepacked Merck silica gel column. Elution was performed with ethyl acetate:cyclohexane, 10:90. 6 Ml. fractions are collected. The appropriate fractions (TLC) are combined and concentrated to dryness. The residue is recrystallized from isopropyl ether to give 3α-hydroxy-17β-methoxy-5α-androstane, m.p. 164°–167°; IR (mull) 3290, 3220, 1120, 1110, 1005 cm$^{-1}$; NMR (CDCl$_3$) 0.72, 0.76, 0.9–2.0, 3.21, 3.3, and 4.01 δ and 3β-hydroxy-17β-methoxy-5α-androstane, m.p. 150°–152°; NMR (CDCl$_3$) 0.75–2.0, 3.25, 3.37 and 3.6 δ.

EXAMPLE 28

3α-Chloro-17β-methoxy-5α-androstane (VII)

A solution of triphenylphosphine (8.22 g.) in THF (80 ml.) is added dropwise to N-chlorosuccinimide (4.18 g.) with stirring and cooling so that the temperature remains below 30°. A solution of 3β-hydroxy-17β-methoxy-5α-androstane (Example 27, 4.8 g.) in THF (50 ml.) is slowly added to the N-chlorosuccinimide mixture. After 2 hours, methanol is added and the mixture is filtered to obtain the title compound (recrystallized from acetone): m.p. 151°–154°; NMR (CDCl$_3$) 0.74, 0.78, 3.20, 3.33 and 4.47 δ; MS (m/e) 324, 309, 277 and 251.

EXAMPLE 29

3β-Chloro-17β-methoxy-5α-androstane (VII)

Following the general procedure of Example 28 and making non-critical variations 3α-hydroxy-17β-methoxy-5α-androstane (Example 27, 0.47 g.) is reacted with N-chlorosuccinimide for 2 hours. The mixture is extracted with SSB, concentrated, and chromatographed on silica gel eluting with ethyl acetate-hexane (5:95) to obtain the title compound, upon recrystallization from methanol, NMR (CDCl$_3$) 0.74, 0.84, 3.16, 3.33 and 3.75 δ; MS (m/e) 324, 309, 292, 277 and 251.

EXAMPLE 30

17β-Methoxy-2'-methyl-5α-androstano[2,3-d]oxazole (VIII)

Step A—17β-Methoxy-2-acetoxymethylene-5α-androstan-3-one

A mixture of 17β-methoxy-2-hydroxymethylen-5α-androstan-3-one (U.S. Pat. No. 3,980,638, Example 3, 0.5 gm.) in acetic anhydride (3.0 ml.) and pyridine (3 ml.) is allowed to stand at 20°–25° for 24 hours. The reaction mixture is then poured into water and the product separates. The product is collected and dissolved in benzene and purified by column chromatography on Florisil. The appropriate fractions (TLC) are pooled and concentrated to give a residue. The residue is crystallized from methanol to give 17β-methoxy-2-acetoxymethylen-5α-androstan-3-one.

Step B—17β-Methoxy-2-hydroxyimino-5α-androstan-3-one

Acetic acid (0.23 gm.) is added dropwise to a mixture of the acetate from Step A (0.25 gm.) in methanol (5 ml.) and sodium nitrite (0.20 gm.), and the mixture is stirred at 20°–25° for 2 hours. The reaction mixture is poured into water (50 ml.) and the precipitate recovered and crystallized from methanol to give the crude 2-hydroxyimino compound.

Step C—17β-Methoxy-2α-acetamidoandrostan-3-one

Zinc dust (7.7 gm.) in small portions is added at room temperature to a suspension of the 2-hydroxyimino compound from Step B (3.85 gm.) in acetic acid-acetic anhydride (1:1) containing anhydrous sodium acetate (0.35 gm.) and mercuric chloride (35 mg.). The mixture is refluxed for 30 minutes and the insoluble material removed by filtration. The residue is washed with acetic acid (20 ml.). The filtrate and washings are combined, diluted with water and extracted with benzene (3×100 ml.). The organic phase is washed with water, dried, and concentrated to give a residue. The residue is column chromatographed on alumina (100 gm.) and successively eluted with benzene, benzene: ether (9:1), ether, ether:ethyl acetate (1:1), and ethyl acetate. The appropriate fractions (TLC) are pooled and concentrated to give the 2α-acetamido compound.

Step D—17β-Methoxy-2'-methyl-5α-androstano[2,3-d]oxazole (VIII)

A mixture of concentrated sulfuric acid (0.2 ml.) and acetic anhydride (10 ml.) is added to a stirred suspension of the 2α-acetamido compound from Step C (1.48 gm.) in acetic anhydride (20 ml.). After the mixture is kept at 20°–25° overnight it is heated at 80° for three hours. The mixture is cooled and diluted with water. The crystals which separate are collected, dissolved in benzene and column chromatographed on alumina (30 gm.). The column is eluted with benzene and benzene-ether (9:1). The appropriate fractions are pooled and concentrated to give the title compound.

EXAMPLE 31

17β-Methoxy-5α-androstano[3,2-c]pyrazole (IX)

A mixture of 17β-methoxy-2-hydroxymethylene-5α-androstan-3-one (U.S. Pat. No. 3,980,638, Example 3, 140 mg.) and hydrazine hydrate (0.2 ml.) in absolute ethanol (10 ml.) is refluxed for 1.5 hours. The mixture is then concentrated to about 2 ml. by a stream of nitrogen. Water is added and a precipitate forms which is filtered, washed with water, and recrystallized from acetone-water to give the title compound, m.p. 227°–230°; MS (m/e) 328, 313, 201 and 96; NMR (CDCl$_3$) 0.74, 0.77, 3.22, 3.35, 5.26 and 7.25 δ; UV (ethanol) λ=224 nm (ε=4,950).

EXAMPLE 32

17β-Methoxy-1'-methyl-5α-androstano[3,2-c]pyrazole (IX) and
17β-methoxy-2'-methyl-5α-androstano[3,2-c]pyrazole (X)

Following the general procedure of Example 31 and making non-critical variations but replacing hydrazine hydrate with methyl hydrazine the title compounds are obtained.

EXAMPLE 33

17β-Methoxy-2'-phenyl-5α-androstano[3,2-c]pyrazole (X) and
17β-methoxy-1'-phenyl-5α-androstano[3,2-c]pyrazole (IX)

A mixture of 17β-methoxy-2-hydroxymethylene-5α-androstan-3-one (U.S. Pat. No. 3,980,638, Example 3, 2.0 g.) and phenyl hydrazine (0.72 g., 0.65 ml.) in absolute ethanol (10 ml.) is refluxed 1.5 hours. The reaction mixture is then concentrated to about ⅓ its volume by reduced pressure and the residue diluted with water. The suspended solid is collected on a filter, washed with water and dried under reduced pressure. The solid is column chromatographed on silica gel (230 g.) eluting with ethyl acetate-cyclohexane (5:95). A first series of homogeneous fractions are pooled and concentrated under reduced pressure to a solid which is recrystallized from ethyl acetate to give the 2'-phenylpyrazole (X), m.p. 213°–221°; MS (m/e) 404; UV (ethanol) λ=268 nm (ε=20,500); IR (mull) 1600, 1575, 1505, 1495, 1380, 1215, 1105, 1045, 995 and 760 cm$^{-1}$.

A second series of homogeneous fractions are pooled and concentrated under reduced pressure to a solid which is recrystallized from ethyl acetate to give the 1'-phenylpyrazole (IX), m.p. 194°–197°; MS (m/e) 404;

UV (ethanol) λ=252 nm (ε=11,450); IR (mull) 1600, 1505, 1395, 1380, 1105, 975, 845, 765 and 695 cm$^{-1}$.

EXAMPLE 34

17β-Methoxy-5'-methyl-5α-androstano[3,2-c]pyrazole (X)

Step A—2-Acetyl-17β-methoxy-5α-androstan-3-one

Following the general procedure of U.S. Pat. No. 3,135,743, Example 12, and making non-critical variations but starting with 17β-methoxy-5α-androstan-3-one (I) in place of 17β-hydroxy-5α-androstane-3-one there is obtained 2-acetyl-17β-methoxy-5α-androstan-3-one.

Step B—17β-Methoxy-5'-methyl-5α-androstano[3,2-c]pyrazole (X)

Following the general procedure of Example 31 and making non-critical variations but starting with 2-acetyl-17β-methoxy-5α-androstan-3-one (Step A) in place of 17β-methoxy-2-hydroxymethylene-5α-androstan-3-one there is obtained the title compound.

EXAMPLE 35

17β-Methoxy-2',5'-dimethyl-5α-androstano[3,2-c]pyrazole (X)

Step A—2-Acetyl-17β-methoxy-5α-androstan-3-one
See Example 34, Step A.

Step B—17β-Methoxy-2',5'-dimethyl-5α-androstano[3,2-c]pyrazole (X)

Following the general procedure of Example 34, Step B, and making non-critical variations but substituting methyl hydrazine for hydrazine hydrate the title compound is obtained.

EXAMPLE 36

17β-Methoxy-5'-methyl-2'-phenyl-5α-androstano[3,2-c]pyrazole (X)

Step A—2-Acetyl-17β-methoxy-5α-androstan-3-one
See Example 34, Step A.

Step B—17β-Methoxy-5'-methyl-2'-phenyl-5α-androstano[3,2-c]pyrazole (X)

Following the general procedure of Example 34, Step B, and making non-critical variation but starting with phenyl hydrazine in place of hydrazine hydrate the title compound is obtained.

EXAMPLE 37

17β-Methoxy-5'-phenyl-5α-androstano[3,2-c]pyrazole (X)

Step A—2-Benzoyl-17β-methoxy-5α-androstan-3-one

Following the general procedure of U.S. Pat. No. 3,135,743, Example 12, but starting with 17β-methoxy-5α-androstan-3-one and using benzoic acid and benzoic acid anhydride in place of acetic acid and acetic anhydride, 2-benzoyl-17β-methoxy-5α-androstan-3-one is obtained.

Step B—17β-Methoxy-5'-phenyl-5α-androstano[3,2-c]pyrazole (X)

Following the general procedure of Example 31 and making non-critical variations but starting with 2-benzoyl-17β-methoxy-5α-androstan-3-one the title compound is obtained.

EXAMPLE 38

17β-Methoxy-2'-methyl-5'-phenyl-5α-androstano[3,2-c]pyrazole (X)

Step A—2-Benzoyl-17β-methoxy-5α-androstan-3-one
See Example 37, Step A.

Step B—17β-Methoxy-2'-methyl-5'-phenyl-5α-androstano[3,2-c]pyrazole (X)

Following the general procedure of Example 33 and making non-critical variations but starting with methyl hydrazine instead of phenyl hydrazine the title compound is obtained.

EXAMPLE 39

17β-Methoxy-2'-methyl-5α-androstano[3,2-d]thiazole (XI)

A mixture of 2α-bromo-17β-methoxy-5α-androstan-3-one (U.S. Pat. No. 3,301,850, Example 15, 2.0 g.) and thioacetamide (0.43 g.) in absolute ethanol (10 ml.) is heated at reflux for 5 hours, allowed to cool, and stirred at 20°–25° for 18 hours. The mixture is then poured into water and the precipitate is extracted twice with chloroform. The combined extracts are washed with water, saline, filtered thru sodium sulfate and concentrated to a residue. The residue is column chromatographed on silica gel (240 g.) eluting with ethyl acetate-cyclohexane (10:90). The appropriate fractions (TLC) are pooled and concentrated to produce a solid which upon recrystallization from isopropyl ether gives the title compound, m.p. 154°–156°; MS (m/e) 359; UV (ethanol) λ=212 nm (ε=2,300); NMR (CDCl$_3$) 0.7-3.2, 2.58 and 3.33 δ; IR (mull) 1565, 1110, 1100 and 1190 cm$^{-1}$.

EXAMPLE 40

2-(1-hydroxy-1-ethylidene)-17β-methoxy-5α-androstan-3-one (XII) and
2-benzoyl-17β-methoxy-5α-androstan-3-one (XII)

See Example 34, Step A, and Example 36, Step A, respectively.

EXAMPLE 41

17β-Methoxy-2'-methyl-5α-androstano[3,2-d]imidazole (XIII)

A mixture of 17β-methoxy-2α-acetamido-5α-androstan-3-one (Example 30, Step C, 0.975 g.) and ammonium acetate (1.92 g.) and acetic acid (15 ml.) is refluxed for six hours. The organic diluent is removed by reduced pressure to leave a residue. Small pieces of ice and ammonium hydroxide (5%) is added to the residue from which a solid separates which is collected, dissolved in benzene, and column chromatographed on alumina (25 g.). Elution is performed with benzene-ether (4:1, 1:1), ether, and ethyl acetate. The appropriate fractions (TLC) are pooled and concentrated to a residue which is recrystallized from acetone to give the title compound.

EXAMPLE 42

17β-Methoxy-5α-androstano[3,2-d]pyrimidine (XIV)

Following the general procedure of U.S. Pat. No. 3,132,137, Example 2, but starting with 17β-methoxy-5α-androstan-3-one instead of 17β-hydroxy-5α-androstan-3-one the title compound is obtained.

EXAMPLE 43

17β-Benzyloxy-2α,3α-epithio-5α-androstane (XV)

Step A—17β-Benzyloxy-17α-methyl-5α-androst-2-ene

Following the general procedure of Example 8(B) and making non-critical variations but starting with 17β-hydroxy-17α-methyl-5α-androst-2-ene and benzyl iodide instead of 17β-hydroxy-17α-methyl-5α-androstan-3-one and methyl iodide, 17β-benzyloxy-17α-methyl-5α-androst-2-ene is obtained.

Step B—17β-Benzyloxy-2β,3β-epoxy-17α-methyl-5α-androstane

Following the general procedure of U.S. Pat. No. 3,682,898, in particular Examples 1 and 2, and making noncritical variations but starting with 17β-benzyloxy-17α-methyl-5α-androst-2-ene, 17β-benzyloxy-2β,3β-epoxy-17α-methyl-5α-androstane is obtained.

Step C—17β-Benzyloxy-2α,3α-epithio-17α-methyl-5α-androstane

Following the general procedure of U.S. Pat. No. 3,682,898, Examples 4 and 7 or U.S. Pat. No. 3,301,850, Examples 1 and 2 and making non-critical variations but starting with 17β-benzyloxy-2β,3β-epoxy-17α-methyl-5α-androstane, 17β-benzyloxy-2α,3α-epithio-17α-methyl-5α-androstane is obtained.

EXAMPLE 44

2α,3α-Epoxy-17β-methoxy-5α-androstane (XV)

Step A—2α,3α-Epoxy-17β-hydroxy-5α-androstane

A solution of sodium borohydride (600 mg.) in ice-cold methanol (10 ml.) is added to a solution of 2α,3α-epoxy-5α-androstan-17-one (U.S. Pat. No. 3,169,136, Example I, 1.34 g.) in methanol (60 ml.) and the mixture is stirred at 0° for 30 minutes. The mixture is washed with saline, dried over sodium sulfate and concentrated under reduced pressure to give a residue which is chromatographed on a silica gel column. Appropriate fractions (TLC) are pooled and concentrated to give 2α,3α-epoxy-17β-hydroxy-5α-androstane.

Step B—2α,3α-Epoxy-17β-methoxy-5α-androstane

Following the general procedure of Example 16 and making non-critical variations but starting with 2α,3α-epoxy-17β-hydroxy-5α-androstane, the title compound is obtained.

EXAMPLE 45

A 70 kg. 25 year old man who demonstrates approximately 100 million apparently normal sperm/ml. of ejaculate is treated twice daily with a tablet containing 10 mg. of 17β-benzyloxy-5α-androstan-3-one (I) for about 100 days. After which time it is found that following sexual intercourse he does not fertilize a fertile female (who has previously delivered a child) at the most fertile time of her period. The steroid is continuously administered to the man twice daily and he remains infertile.

EXAMPLE 46

An 80 kg. 22 year old man who demonstrates approximately 90 million apparently normal sperm/ml. of ejaculate is treated with a 200 mg. capsule of 17β-hexadecanoxy-5α-androstan-3-one (I) four times daily for 60 days. After which time it is found that following sexual intercourse he does not fertilize a fertile female (who has previously delivered a child) at the most fertile time of her period. The steroid is continuously administered to the man 4 times daily and he remains infertile.

EXAMPLE 47

A 70 kg. 30 year old man who demonstrates approximately 95 million apparently normal sperm/ml. of ejaculate is given one-half teaspooonful/day of an elixir of 17β-n-heptanoxy-5α-androstan-3-one (I) (100 mg./ml.). After 60 days it is found that following sexual intercourse he does not fertilize a fertile female (who has previously delivered a child) at the most fertile time of her period. Upon continued administration of the same amount of the elixir he remains infertile.

EXAMPLE 48

A 60 kg. 26 year old man who is the admitted father of 2 children is given one 50 mg. tablet of 17β-(2-propenyloxy)-5α-androstan-3-one (I) daily. After 60 days it is found that following sexual intercourse he does not fertilize the mother of his 2 children at the most fertile time of her period. The steroid is continuously administered daily and he remains infertile.

EXAMPLE 49

A 60 kg. 20 year old man is given one teaspoonful of a suspension of 17α-ethinyl-17β-methoxy-2α-methyl-5α-androstan-3-one (I) (100 mg./ml.) daily. After 60 days it is found that following sexual intercourse he does not fertilize a fertile female (who has previously delivered a child) at the most fertile time of her period. Upon continuous daily administration the patient remains infertile.

EXAMPLE 50

A 6 kg. tom who has previously sired offspring is given a treat daily containing 20 mg. of 17α-ethinyl-17β-(2-propenyloxy)-5α-androstan-3-one (I). After 60 days it is found that following sexual intercourse the animal does not fertilize an ovulating female (who has previously delivered kittens) at the time of her estrus. Upon continuous daily administration of the treat to the tom the animal remains infertile. Eighty days following cessation of administration of the treat, the tom upon sexual intercourse fertilized the same ovulating female at the time of her estrus.

EXAMPLE 51

A 10 kg. dog who has previously sired offspring is treated by adding 17α-ethinyl-17β-methoxy-5α-androstan-3-one (I) to its daily food ration as follows: a veterinary premix containing 2% of the active ingredient is added to the animal's daily normal dietary intake such that it provides sufficient quantity of the active material for contraceptive purposes. In the particular case, using a 2% veterinary premix 5 g. of the premix delivers 100 mg. of the contraceptive agent which provides for 10 mg./kg./day. After feeding 60 days of this type of diet it is found that following sexual intercourse the animal does not fertilize an ovulating female (who has previously delivered young) at the time of her estrus.

In addition to the active ingredient the veterinary premix includes liver protein, whole liver powder, fish meal, terra alba dicalcium phosphate, ferrous glucanate powder, wheat germ oil, and brewer's yeast in sufficient quantity to provide a veterinary premix containing 2% of the active ingredient.

Following the general procedure of Examples 45-51 and making non-critical variations but substituting the compounds of Column A for the compounds used in Examples 45-51 the same reversible contraceptive effect is obtained.

| Ex. | Column A |
|---|---|
| 52 | 17β-methoxy-17α-methyl-5α-androstan-3-one (I) |
| 53 | 17α-methyl-17β-(2-propenyloxy)-5α-androstan-3-one (I) |
| 54 | 4',5'-dihydrospiro[5α-androstan-17,2'(3H)furan]-3-one (I) |
| 55 | 17β-benzyloxy-2α-methyl-5α-androstan-3-one (I) |
| 56 | 2α-ethyl-17β-methoxy-5α-androstan-3-one (I) |
| 57 | 17β-methoxy-2,2-dimethyl-5α-androstan-3-one (I) |
| 58 | 17β-methoxy-2α-methyl-5α-androstan-3-one oxime (I) |
| 59 | 17β-methoxy-7β-methylandrost-4-en-3-one (I) |
| 60 | 17β-methoxy-2α,7β-dimethylandrost-4-en-3-one (I) |
| 61 | 17α-ethinyl-17β-methoxyandrost-4-en-3-one (I) |
| 62 | 17β-methoxy-2α-methylandrost-4-en-3-one (I) |
| 63 | 17β-methoxy-2-spirocyclopropyl-5α-androstan-3-one (II) |
| 64 | 17β-methoxy-1α,2α-methylene-5α-androstan-3-one (III) |
| 65 | 17β-methoxy-5α-androst-1-en-3-one (IV) |
| 66 | 17β-methoxy-2-methylandrost-1-en-3-one (IV) |
| 67 | 17β-methoxy-5α-androstan-2-one (V) |
| 68 | 2α-chloro-17β-methoxy-5α-androstan-3-one (VI) |
| 69 | 3α-chloro-17β-methoxy-5α-androstane (VII) |
| 70 | 3β-chloro-17β-methoxy-5α-androstane (VII) |
| 71 | 17β-methoxy-2'-methyl-5α-androstano-[2,3-d]oxazole (VIII) |
| 72 | 17β-methoxy-5α-androstano[3,2-c]pyrazole (IX) |
| 73 | 17β-methoxy-1'-methyl-5α-androstano-[3,2-c]pyrazole (IX) |
| 74 | 17β-methoxy-2'-methyl-5α-androstano-[3,2-c]pyrazole (X) |
| 75 | 17β-methoxy-2'-phenyl-5α-androstano-[3,2-c]pyrazole (X) |
| 76 | 17β-methoxy-1'-phenyl-5α-androstano-[3,2-c]pyrazole (IX) |
| 77 | 17β-methoxy-5'-methyl-5α-androstano-[3,2-c]pyrazole (X) |
| 78 | 17β-methoxy-2',5'-dimethyl-5α-androstano-[3,2-c]pyrazole (X) |
| 79 | 17β-methoxy-5'-methyl-2'-phenyl-5α-androstano[3,2-c]pyrazole (X) |
| 80 | 17β-methoxy-5'-phenyl-5α-androstano-[3,2-c]pyrazole (X) |
| 81 | 17β-methoxy-2'-methyl-5'-phenyl-5α-androstano[3,2-c]pyrazole (X) |
| 82 | 17β-methoxy-2'-methyl-5α-androstano-[3,2-d]thiazole (XI) |
| 83 | 2-(1-hydroxy-1-ethylidene)-17β-methoxy-5α-androstan-3-one (XII) |
| 84 | 17β-methoxy-2'-methyl-5α-androstano-[3,2-d]imidazole (XIII) |
| 85 | 17β-methoxy-5α-androstano[3,2-d]-pyrimidine (XIV) |
| 86 | 17β-benzyloxy-2α,3α-epithio-17α-methyl-5α-androstane (XV) |
| 87 | 2α,3α-epoxy-17β-methoxy-5α-androstane (XV) |

We claim:

1. A method of effecting male contraception which comprises oral administration of a contraceptively effective amount of a comound of the formula:

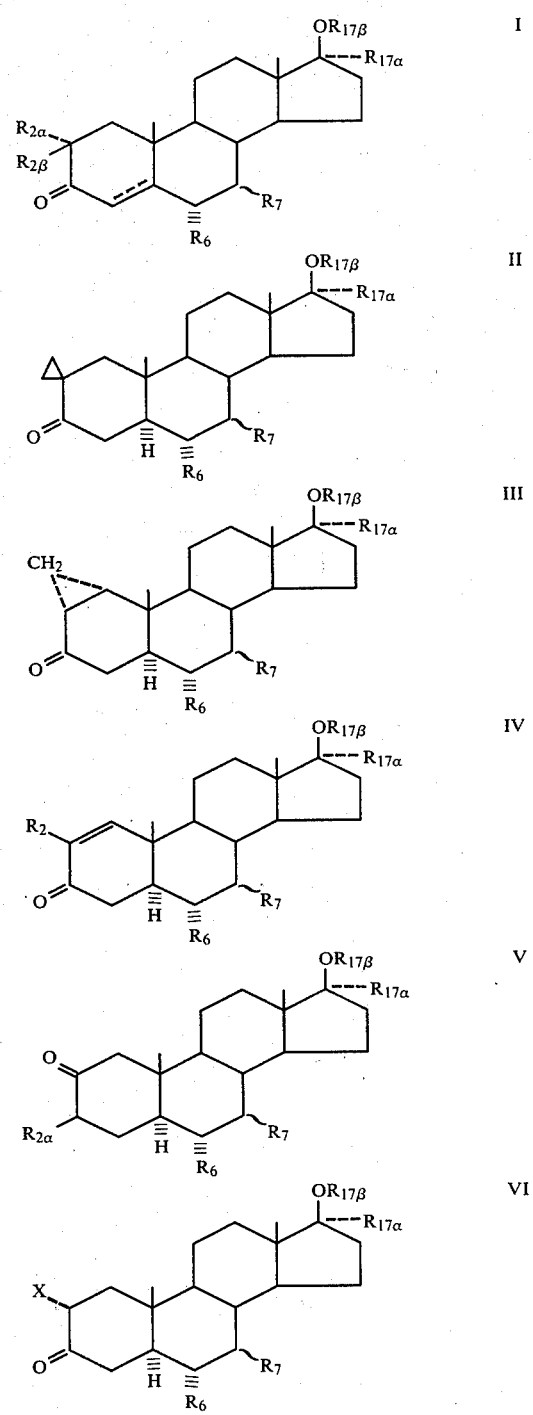

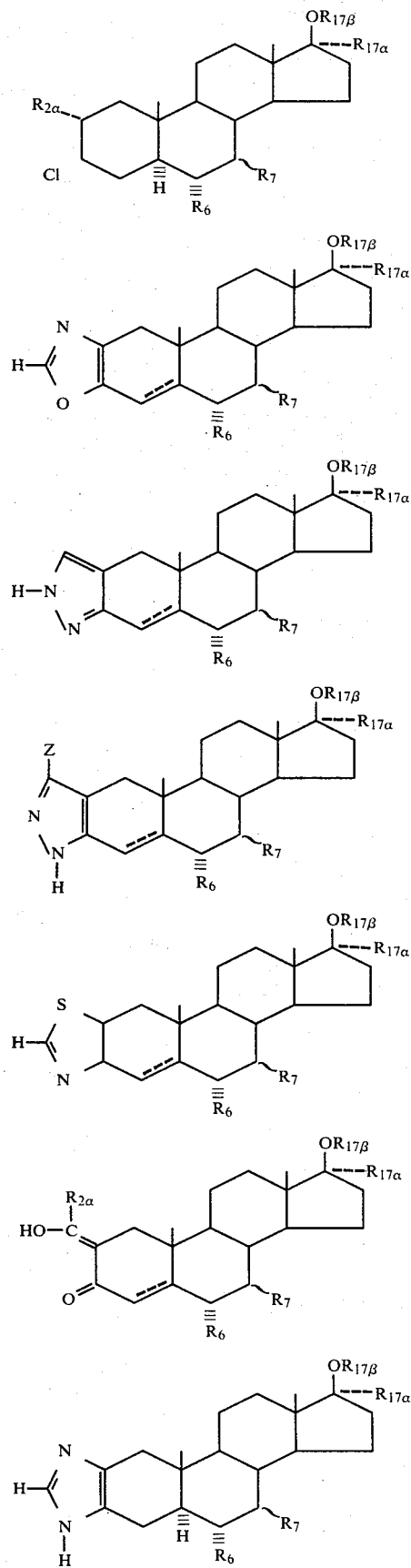

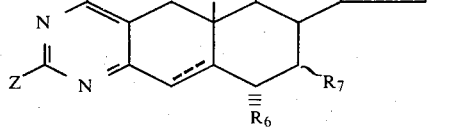

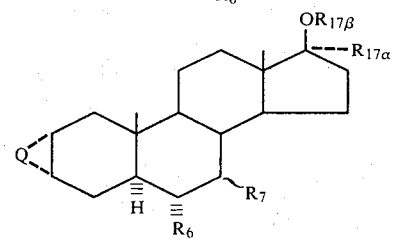

where A is a methyl, methoxy, trifluoromethyl, hydroxyl or nitro group or a hydrogen, fluorine, chlorine or bromine atom; where D is a methyl, methoxy, trifluoromethyl, hydroxyl or nitro group or a hydrogen, fluorine, chlorine or bromine atom; where M is a methyl, methoxy, trifluoromethyl, hydroxyl or nitro group or a hydrogen, fluorine, chlorine or bromine atom; where $R_2$ is a hydrogen atom or methyl group; where $R_{2\alpha}$ is a hydrogen atom, alkyl 1 thru 4 carbon atoms or benzyl; where $R_{2\beta}$ is a hydrogen atom or methyl group with the proviso that when $R_{2\beta}$ is methyl, $R_{2\alpha}$ is also methyl; where $R_{2\alpha}$ is alkyl of 1 thru 3 carbon atoms or

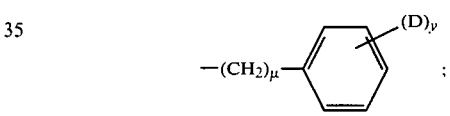

where $R_3$ is alkyl of 1 thru 4 carbon atoms or phenyl; where $R_6$ is a hydrogen atom or methyl group; where $R_7$ is a hydrogen atom or methyl group; where $R_{17\alpha}$ is a hydrogen atom, alkyl of 1 thru 4 carbon atoms, alkenyl of 2 thru 4 carbon atoms or alkynyl of 2 thru 4 carbon atoms; where $R_{17\beta}$ is alkyl of 1 thru 16 carbon atoms,

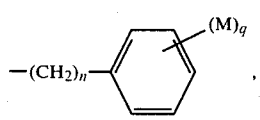

—$(CH_2)_n$—$CH(CH_2)_m$, —$CH_2$—alkenyl where alkenyl is 2 thru 15 carbon atoms or —$CH_2$—$C\equiv CH$, and $R_{17\alpha}$ and $R_{17\beta}$ can be connected to form a cyclic ether containing 4 or 5 carbon atoms; where Q is an oxygen atom; where X is a fluorine, chlorine or bromine atom; where Z is a hydrogen atom, alkyl of 1 thru 4 carbon atoms or

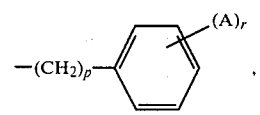

that for the compounds of formula (XIV) the Z's may be the same or different; where m is 4 thru 6; where n is 0 thru 4; where p is 0 thru 4; where q is 1 or 2, when q is 2 the M's can be the same or different; where r is 1 or 2, when r is 2 the A's can be the same or different; where y is 1 or 2, when y is 2 the D's can be the same or different; where $\mu$ is 0 thru 4; where ∼ indicates the attached group can be in either the $\alpha$ or $\beta$ configuration; and where --- is a single or double bond, if a single bond the hydrogen atom at $C_5$ is $\alpha$; including the oximers and O-substituted oximes of compounds I thru IV and VI made with $NH_2$—$OR_3$ to a male mammal postpuberty selected from the group consisting of man, male dog, tom, bull, stallion, ram, boar, male rat, and male mouse.

2. A method according to claim 1 where the contraceptively effective amount is 0.01–15 mg./kg./day.

3. A method of male contraception according to claim 2 where the compound is a compound of formula (I).

4. A method of male contraception according to claim 2 where the compound is a compound of formula (II).

5. A method of male contraception according to claim 2 where the compound is a compound of formula (III).

6. A method of male contraception according to claim 2 where the compound is a compound of formula (IV).

7. A method of male contraception according to claim 2 where the compound is a compound of formula (V).

8. A method of male contraception according to claim 2 where the compound is a compound of formula (VI).

9. A method of male contraception according to claim 2 where the compound is a compound of formula (VII).

10. A method of male contraception according to claim 2 where the compound is a compound of formula (VIII).

11. A method of male contraception according to claim 2 where the compound is a compound of formula (IX).

12. A method of male contraception according to claim 2 where the compound is a compound of formula (X).

13. A method of male contraception according to claim 2 where the compound is a compound of formula (XI).

14. A method of male contraception according to claim 2 where the compound is a compound of formula (XII).

15. A method of male contraception according to claim 2 where the compound is a compound of formula (XIII).

16. A method of male contraception according to claim 2 where the compound is a compound of formula (XIV).

17. A method of male contraception according to claim 2 where the compound is a compound of formula (XV).

* * * * *

Disclaimer 4,297,350.—*John C. Babcock;* and *Allan Campbell,* Kalamazoo, and *Thomas J. Lobi,* Portage, Mich. MALE CONTRACEPTIVE STEROIDS AND METHODS OF USE. Patent dated Oct. 27, 1981. Disclaimer filed May 15, 1982, by the assignee, *The Upjohn Co.*

Hereby enters this disclaimer to claims 192, 194-196 and 198-203 of said patent.

*[Official Gazette June 29, 1982.]*